United States Patent
Nam et al.

(10) Patent No.: US 9,949,702 B2
(45) Date of Patent: Apr. 24, 2018

(54) X-RAY GRID STRUCTURE AND X-RAY APPARATUS INCLUDING THE SAME

(71) Applicant: SAMSUNG ELECTRONICS CO., LTD., Suwon-si (KR)

(72) Inventors: Jae-won Nam, Yongin-si (KR); Kyung-jun Noh, Suwon-si (KR); Seung-hwan Lee, Seoul (KR); Dae-woong Han, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 273 days.

(21) Appl. No.: 14/628,509

(22) Filed: Feb. 23, 2015

(65) Prior Publication Data

US 2015/0243398 A1  Aug. 27, 2015

(30) Foreign Application Priority Data

Feb. 21, 2014 (KR) .................... 10-2014-0020816
Aug. 20, 2014 (KR) .................... 10-2014-0108457

(51) Int. Cl.
| | | |
|---|---|---|
| *A61B 6/00* | (2006.01) | |
| *G21K 1/02* | (2006.01) | |
| *G21K 1/10* | (2006.01) | |
| *G01N 23/04* | (2018.01) | |
| *G21K 5/08* | (2006.01) | |

(52) U.S. Cl.
CPC .......... *A61B 6/4291* (2013.01); *A61B 6/4405* (2013.01); *A61B 6/4411* (2013.01); *G01N 23/04* (2013.01); *G21K 1/02* (2013.01); *G21K 1/025* (2013.01); *G21K 1/10* (2013.01); *G21K 5/08* (2013.01)

(58) Field of Classification Search
CPC ... A61B 6/4291; A61B 6/4405; A61B 6/4411; G21K 1/02; G21K 1/025
USPC ............... 378/19, 98.8, 147, 154, 155, 149; 250/370.09
See application file for complete search history.

(56) References Cited

U.S. PATENT DOCUMENTS

| | | | | |
|---|---|---|---|---|
| 5,357,553 A | * | 10/1994 | Ferlic ............... | G21K 1/025 378/154 |
| 5,721,761 A | * | 2/1998 | Ferlic ............... | G21K 1/025 378/145 |
| 5,991,357 A | * | 11/1999 | Marcovici ......... | A61B 6/035 250/370.09 |

(Continued)

FOREIGN PATENT DOCUMENTS

| | | |
|---|---|---|
| JP | 2010-243564 A | 10/2010 |
| WO | 2007-061152 A1 | 7/2015 |

OTHER PUBLICATIONS

Communication dated Jul. 23, 2015 issued by the European Patent Office in counterpart European Patent Application No. 15155377.3.

*Primary Examiner* — Allen C. Ho
(74) *Attorney, Agent, or Firm* — Sughrue Mion, PLLC

(57) ABSTRACT

An X-ray grid structure is configured to be detachably attached to an X-ray detector and includes an X-ray grid configured to selectively transmit X-rays; and holders fixed along an outer edge of the X-ray grid, wherein at least one of the holders includes an elastic material and is configured to be bendable in a direction crossing an attachment direction, which is a direction of attaching the X-ray detector to the X-ray grid.

25 Claims, 23 Drawing Sheets

(56) References Cited

U.S. PATENT DOCUMENTS

| | | | | |
|---|---|---|---|---|
| 6,055,296 | A * | 4/2000 | Ferlic | G21K 1/025 378/145 |
| 6,064,720 | A * | 5/2000 | Piscitelli | A61B 6/00 378/154 |
| 6,175,615 | B1 * | 1/2001 | Guru | G21K 1/025 378/147 |
| 6,365,900 | B1 * | 4/2002 | Mestais | G01T 1/1642 250/363.1 |
| 6,396,898 | B1 * | 5/2002 | Saito | G01N 23/046 378/19 |
| 6,587,538 | B2 * | 7/2003 | Igarashi | A61B 6/06 250/367 |
| 6,778,637 | B2 * | 8/2004 | Luhta | G21K 1/025 250/363.1 |
| 6,993,110 | B2 * | 1/2006 | Hoffman | G21K 1/025 250/363.1 |
| 7,019,300 | B2 * | 3/2006 | Watanabe | G01T 1/2928 250/370.08 |
| 7,177,387 | B2 * | 2/2007 | Yasunaga | A61B 6/032 250/370.09 |
| 7,180,073 | B2 * | 2/2007 | Tetsuo | G01T 1/2928 250/370.08 |
| 7,190,759 | B2 * | 3/2007 | Ratzmann | A61B 6/035 250/370.09 |
| 7,235,790 | B2 * | 6/2007 | Hoge | G01T 1/1648 250/370.09 |
| 7,236,560 | B2 * | 6/2007 | Malamud | A61B 6/032 250/505.1 |
| 7,257,195 | B2 * | 8/2007 | Freund | G21K 1/025 378/147 |
| 7,339,176 | B2 * | 3/2008 | El-Hanany | G01T 1/2928 250/370.09 |
| 7,418,082 | B2 * | 8/2008 | Levene | G21K 1/025 378/147 |
| 7,492,857 | B2 * | 2/2009 | Yasunaga | A61B 6/032 250/370.09 |
| 7,503,693 | B2 * | 3/2009 | Jährling | G01T 1/02 378/205 |
| 7,525,097 | B2 * | 4/2009 | Dorscheid | G01T 1/2018 250/370.09 |
| 7,560,702 | B2 * | 7/2009 | Meirav | A61B 6/032 250/370.09 |
| 7,564,940 | B2 * | 7/2009 | Mattson | A61B 6/032 250/370.09 |
| 7,783,000 | B2 * | 8/2010 | Kotooka | A61B 6/032 250/370.09 |
| 7,787,596 | B2 * | 8/2010 | Hempel | G01N 23/046 378/145 |
| 7,857,511 | B2 * | 12/2010 | Hesl | A61B 6/4233 378/189 |
| 7,869,573 | B2 * | 1/2011 | Banchieri | G21K 1/025 378/147 |
| 8,080,803 | B2 * | 12/2011 | Freund | G01T 1/243 250/370.09 |
| 8,126,119 | B2 * | 2/2012 | Kurochi | A61B 6/06 378/147 |
| 8,160,207 | B2 * | 4/2012 | Watanabe | A61B 6/06 378/154 |
| 8,172,461 | B2 * | 5/2012 | Liu | A61B 6/4283 378/114 |
| 8,243,881 | B2 * | 8/2012 | Kuwabara | A61B 6/5282 378/98.4 |
| 8,256,957 | B1 * | 9/2012 | Barnes | G01T 7/00 378/154 |
| 8,306,182 | B2 * | 11/2012 | Yaoi | A61B 6/035 250/370.09 |
| 8,411,823 | B2 * | 4/2013 | Tonami | A61B 6/4291 250/505.1 |
| 8,451,977 | B2 * | 5/2013 | Kurochi | G21K 1/025 378/147 |
| 8,483,362 | B2 * | 7/2013 | Freund | G21K 1/025 378/147 |
| 8,536,552 | B2 * | 9/2013 | Freund | G01T 1/1648 250/370.09 |
| 8,714,817 | B2 * | 5/2014 | Oyaizu | G03B 42/04 378/189 |
| 8,721,176 | B2 * | 5/2014 | McBroom | A61B 6/4283 378/189 |
| 8,744,049 | B2 * | 6/2014 | Kuwabara | B32B 37/1284 250/397 |
| 8,768,032 | B2 * | 7/2014 | Basu | G06T 11/005 250/559.05 |
| 8,817,946 | B2 * | 8/2014 | Kobayashi | A61B 6/032 250/366 |
| 8,831,181 | B2 * | 9/2014 | Kreisler | A61B 6/032 378/154 |
| 8,848,876 | B2 * | 9/2014 | Kuwabara | A61B 6/4291 378/154 |
| 8,859,070 | B2 * | 10/2014 | Yasuda | B32B 3/08 428/201 |
| 8,861,685 | B2 * | 10/2014 | Pohan | A61B 6/032 378/154 |
| 8,873,705 | B2 * | 10/2014 | Konno | A61B 6/032 378/19 |
| 8,890,079 | B2 * | 11/2014 | Kurochi | G21K 1/025 250/363.1 |
| 8,987,675 | B2 * | 3/2015 | Kato | A61B 6/4429 250/363.1 |
| 9,020,093 | B2 * | 4/2015 | Kurochi | G21K 1/025 378/18 |
| 9,064,611 | B2 * | 6/2015 | Freund | G21K 1/025 |
| 9,261,611 | B2 * | 2/2016 | Shahar | G01T 1/1648 |
| 9,263,160 | B2 * | 2/2016 | Kang | G21K 1/025 |
| 9,320,476 | B2 * | 4/2016 | Iso | A61B 6/03 |
| 9,551,675 | B2 * | 1/2017 | Yu | G21K 1/025 |
| 9,601,223 | B2 * | 3/2017 | Deych | G21K 1/025 |
| 9,620,256 | B2 * | 4/2017 | Virshup | G21K 1/025 |
| 2008/0159486 | A1 | 7/2008 | Hesl et al. | |
| 2012/0076266 | A1 | 3/2012 | Kim et al. | |
| 2013/0070906 | A1 * | 3/2013 | Suwa | A61B 6/4405 378/177 |
| 2013/0077760 | A1 | 3/2013 | Tagawa | |

* cited by examiner

X-RAY GRID STRUCTURE AND X-RAY APPARATUS INCLUDING THE SAME

CROSS-REFERENCE TO RELATED APPLICATION

This application claims priorities from Korean Patent Application No. 10-2014-0020816, filed on Feb. 21, 2014, in the Korean Intellectual Property Office and Korean Patent Application No. 10-2014-0108457, filed on Aug. 20, 2014, in the Korean Intellectual Property Office, the disclosure of which is incorporated herein in its entirety by reference.

BACKGROUND

1. Field

Apparatuses and methods consistent with exemplary embodiments relate to an X-ray grid structure for an X-ray detector, and an X-ray apparatus including the X-ray grid structure.

2. Description of the Related Art

X-ray apparatuses are used as medical imaging apparatuses for obtaining medical images of an object by passing X-rays through the person's body. Such X-ray apparatuses are operated based on X-rays passing through a human body that are absorbed at different rates in different types of tissue. X-ray apparatuses are relatively simple and fast in taking medical images of objects (e.g., patients) as compared with other medical imaging apparatuses such as magnetic resonance imaging (MRI) apparatuses and computerized tomography (CT) apparatuses.

When X-rays pass through a human body, some of the X-rays may be absorbed in the human body, and some of the X-rays may scatter in directions different from the direction in which the X-rays are incident on the human body.

Such scattering of rays may lower the quality of X-ray images. To prevent such deterioration of image quality, X-ray grids which selectively transmit X-rays may be used. If an X-ray grid is disposed between a human body and an X-ray detector, the influence of scattering rays may be minimized.

The use of an X-ray grid may be determined according to the part of a human body to be X-rayed. For example, when a person's chest is X-rayed, an X-ray grid may be used because a large number of X-rays is scattered. However, when a relatively thin part of a person such as a hand or foot is X-rayed, an X-ray grid does not need to be used because a smaller number of X-rays is scattered.

Therefore, before taking an X-ray image, an operator may attach or detach an X-ray grid to or from an X-ray detector according to characteristics of an object to be X-rayed.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments include an X-ray grid structure which is light and easily attachable to an X-ray detection unit, and an X-ray apparatus including the X-ray grid structure.

One or more exemplary embodiments include an X-ray grid structure including a plurality of holders which are simple and easy to manufacture, and an X-ray apparatus including the X-ray grid structure.

According to an aspect of an exemplary embodiment, there is provided an X-ray grid structure configured to be detachably attached to an X-ray detector, the X-ray grid structure including an X-ray grid configured to selectively transmit X-rays, and holders fixed along an outer edge of the X-ray grid, wherein at least one of holders includes an elastic material and is configured to bendable in a direction crossing an attachment direction, which is a direction of attaching the X-ray detector to the X-ray grid.

Holders may be spaced apart from each other along the outer edge of the X-ray grid.

The elastic material may include at least one of polyurethane and silicone.

The at least one of holders may have a hardness of about 70 to about 95 as measured by a Shore A durometer.

The at least one of the holders may include a fixing portion fixed to the X-ray grid, and a support portion configured to be detachably attached to the X-ray detector and configured to support the X-ray detector.

The X-ray detector may include a front side facing the X-ray grid, a rear side opposite the front side, and a lateral side between the front and rear sides, and wherein the support portion may include a side support portion configured to support the lateral side of the X-ray detector, and a rear support portion configured to support the rear side of the X-ray detector.

The rear support portion may have a length of about 3 mm to about 6 mm.

The fixing portion may be fixed to the X-ray grid using an adhesive.

The fixing portion may include a slope, so that a height of the fixing portion increases in an outward direction from a center portion of the X-ray grid.

The rear support portion may include a slope, so that a height of the rear support portion increases in an outward direction from a center of the X-ray grid.

All of the holders may have a same shape and are formed of the same elastic material.

The X-ray grid may have a rectangular shape, and the holders may be disposed at corners of the X-ray grid.

When the X-ray grid structure is attached to the X-ray detector, edges of the X-ray grid may be disposed inward from the outer edge of the X-ray detector with respect to a center portion of the X-ray grid.

The X-ray grid may include a rear side facing the X-ray detector and a front side opposite to the rear side, and reinforcement films disposed on the front side and the rear side of the X-ray grid to reinforce the X-ray grid.

The reinforcement films may include carbon fiber.

The X-ray grid may include a front side facing the X-ray detector and a rear side opposite to the front side, and at least one of the holders may include: a first member contacting the rear side of the X-ray grid; a second member contacting the front side of the X-ray grid; and a coupling member fastening the first member and the second member together.

The first member may include at least one coupling hole structure protruding toward the second member for coupling with the coupling member.

The second member may include a connection hole receiving the coupling member and connected to the coupling hole structure.

The coupling member may include a body portion coupled to the coupling hole structure and a head portion for pressing the second member.

The body portion may include a threaded region screwed into the coupling hole structure and a non-threaded region on which a thread is not formed.

The second member may include an elastic material.

The first member may include a material different from a material included in the second member.

The first member may have bending strength greater than that of the second member.

According to an aspect of another exemplary embodiment, there is provided an X-ray apparatus including an X-ray radiation unit configured to emit X-rays, an X-ray detector configured to detect the X-rays having passed through an object, and an X-ray grid structure which is configured to be detachably attached to the X-ray detector, and includes an X-ray grid configured to selectively transmit X-rays, and holders fixed along an outer edge of the X-ray grid, wherein at least one of holders includes an elastic material and is configured to bend in a direction crossing an attachment direction which is a direction of attaching the X-ray detector to the X-ray grid.

The X-ray apparatus may further include wheels configured to move the X-ray apparatus.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
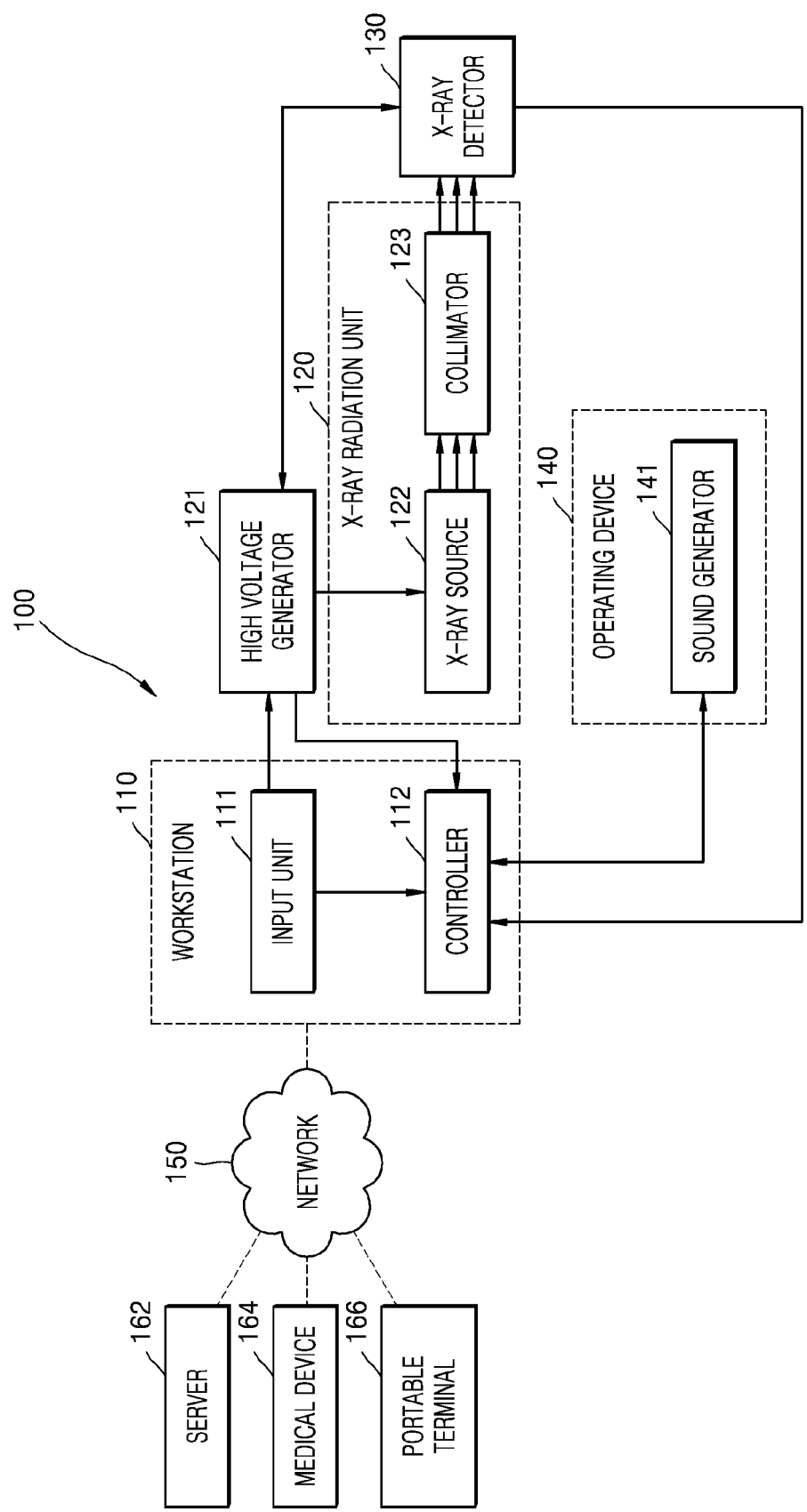
FIG. 1 is a view illustrating an X-ray apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

Hereinafter, structures and operations of an X-ray grid structure and an X-ray apparatus including the X-ray grid structure will be described in detail with reference to the accompanying drawings according to exemplary embodiments. In the following descriptions of the exemplary embodiments, although the terms first, second, third, and fourth are used to describe various elements, these elements should not be limited by these terms. These terms are only used to distinguish one element from other elements.

In the present disclosure, the term "image" may refer to multi-dimensional image data including discrete image elements (for example, pixels of two-dimensional images, and voxels of three-dimensional images).

Furthermore, in the present disclosure, the term "object" may refer to a person, an animal, a person's part, an animal's part, or the like. For example, the term "object" may refer to blood vessels or an organ such as the liver, the heart, the uterus, the brain, the breasts, and the abdomen. Furthermore, the term "object" may refer to a phantom. The phantom is an object having a density, volume, and effective atomic number similar to those of a living organism. For example, the phantom may be a sphere object having features similar to those of a human body.

Furthermore, in the present disclosure, the term "operator" may refer to a medical service person such as doctors, nurses, medical laboratory technologists, medical imaging technicians, and medical equipment repairmen. However, the term "operator" is not limited thereto.

FIG. 1 is a view illustrating an X-ray apparatus 100 according to an exemplary embodiment. The X-ray apparatus 100 of FIG. 1 may be a fixed or movable X-ray apparatus.

Referring to FIG. 1, the X-ray apparatus 100 may include a workstation 110, an X-ray radiation unit 120, a high voltage generator 121, and an X-ray detector 130.

The workstation 110 includes an input unit 111 and a controller 112. An operator may input commands such as an X-ray radiation command for operating the X-ray apparatus 100, and the controller 112 may controls overall operations of the X-ray apparatus 100.

The high voltage generator 121 generates a high voltage and applies the high voltage to an X-ray source 122 to generate X-rays.

The X-ray radiation unit 120 includes the X-ray source 122 configured to receive the high voltage from the high voltage generator 121 and emit X-rays; and a collimator 123 configured to guide X-rays emitted from the X-ray source 122.

The X-ray detector 130 detects X-rays emitted from the X-ray radiation unit 120 and passing through an object.

The X-ray apparatus 100 may further include an operating device 140, and the operating device 140 may include a sound generator 141 configured to generate sounds under the control of the controller 112 so as to provide information about imaging procedures such as X-ray radiation.

The workstation 110, the X-ray radiation unit 120, the high voltage generator 121, and the X-ray detector 130 may be connected to one another through wires or wirelessly. In the latter case, clock synchronization devices may be used.

Examples of the input unit 111 may include a keyboard, a mouse, a touchpad, a speech recognizing device, a fingerprint reader, an iris recognizing device, and any other input devices known to those of ordinary skill in the related art. An operator may input an X-ray radiation command through the input unit 111, and the input unit 111 may include a switch to receive such commands.

If the input unit 111 generates a radiation signal, the controller 112 may signal the sound generator 141 to generate a sound to inform an object of X-ray radiation. In addition, the sound generator 141 may generate other sounds to provide information about other imaging procedures. In FIG. 1, the sound generator 141 is included in the operating device 140. However, the exemplary embodiments are not limited thereto. For example, the sound generator 141 may be disposed in a unit other than the operating device 140. For example, the sound generator 141 may be included in the workstation 110 or may be disposed on a wall of an X-ray room in which an object is x-rayed.

The controller 112 controls the positions of the X-ray radiation unit 120 and the X-ray detector 130, imaging timing, and other imaging conditions according to imaging conditions set by an operator.

In detail, the controller 112 may control the high voltage generator 121 and the X-ray detector 130 according to a command input through the input unit 111, so as to adjust the timing, intensity, and range of X-ray radiation.

In addition, the controller 112 generates X-ray images of an object by using image data received from the X-ray detector 130. In detail, if the controller 112 receives image data of an object from the X-ray detector 130, the controller 112 may remove noise from the image data and may control the dynamic range and interleaving of the image data to generate an X-ray image of the object.

The X-ray apparatus 100 of FIG. 1 may further include an output unit to output an X-ray image generated by the controller 112. In addition, the output unit may output a user interface (UI) and information such as user or object information that may be used to manipulate the X-ray apparatus 100. Examples of the output unit may include a printer, a CRT display, an liquid crystal display (LCD), a plasma display panel (PDP) display, an organic light emitting diode (OLED) display, a field emission display (FED), a light emitting diode (LED) display, a vacuum fluorescent display (VFD), a digital light processing (DLP) display, a primary flight display (PFD), a 3D display, a transparent display, and any other output device known to those of ordinary skill in the related art.

The workstation 110 shown in FIG. 1 may further include a communicator capable of communicating with devices such as a server 162, a medical device 164, and a portable terminal 166 through a network 150.

The communicator may be connected to the network 150 through a wired or wireless connection for communicating with the server 162, the medical device 164, or the portable terminal 166. The communicator may transmit diagnosis data of an object through the network 150. In addition, the communicator may receive medical images captured by the medical device 164 (e.g., a computerized tomography (CT) device, a magnetic resonance imaging (MRI) device, and an X-ray device) through the network 150. Furthermore, the communicator may receive data such as patient diagnosis history data and treatment schedule data from the server 162, and the data may be used for diagnosing an object. In addition, the communicator may exchange data with the portable terminal 166 (e.g., doctor's or user's cellular phones, personal digital assistants (PDAs), or laptop computers) as well as the server 162 and the medical device 164 that may be disposed in a hospital.

The communicator may include at least one module for communicating with external devices. Examples of the module may include a short-distance communication module, a wired communication module, and a wireless communication module.

The short-distance communication module is a module for communicating with other devices located within a certain range of distance. Near field communication technology such as wireless LAN, Wi-Fi, Bluetooth, Zigbee, Wi-Fi direct (WFD), ultra wideband (UWB), infrared data association (IrDA), Bluetooth low energy (BLE), and near field communication (NFC) may be used in exemplary embodiments. However, the exemplary embodiments are not limited thereto.

The wired communication module is a communication module using electric or optical signals. Examples of wired communication technology that may be used in exemplary embodiments include communication technology using pair cables, coaxial cables, or optical fiber cables, and other communication technology known to those of ordinary skill in the related art.

The wireless communication module may transmit/receive wireless signals to/from at least one of a base station, an external device, and a server through a mobile radio communication network. Such wireless signals may be voice call signals, video call signals, or text/multimedia message signals, and thus may include various types of data.

The X-ray apparatus 100 of FIG. 1 may include a plurality of digital signal processors (DSPs), a microprocessing unit, and a special processing circuit (such as a circuit for high-speed A/D conversion, high-speed Fourier transform, or array processing).

The workstation 110 may communicate with the X-ray radiation unit 120, the high voltage generator 121, and the X-ray detector 130 by high-speed digital interfacing such as low voltage differential signaling (LVDS), an asynchronous serial communication method using a universal asynchronous receiver transmitter (UART), a synchronous communication method, a communication method based on a low delay network protocol such as controller area network (CAN), or other communication methods known to those of ordinary skill in the related art.

Figure 2A:
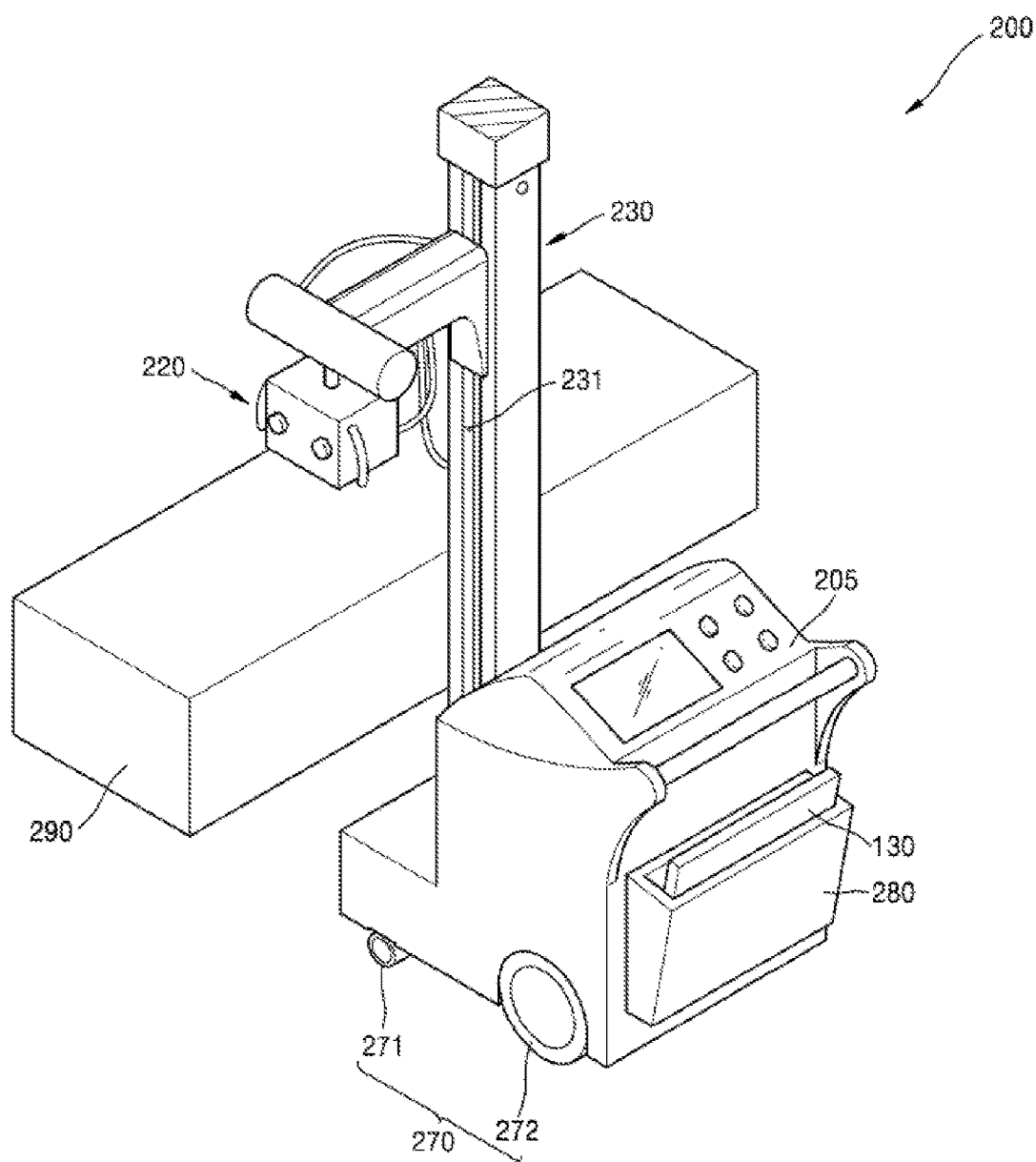
FIG. 2A is a schematic view illustrating an exemplary X-ray apparatus according to an exemplary embodiment.
Figure 2B:
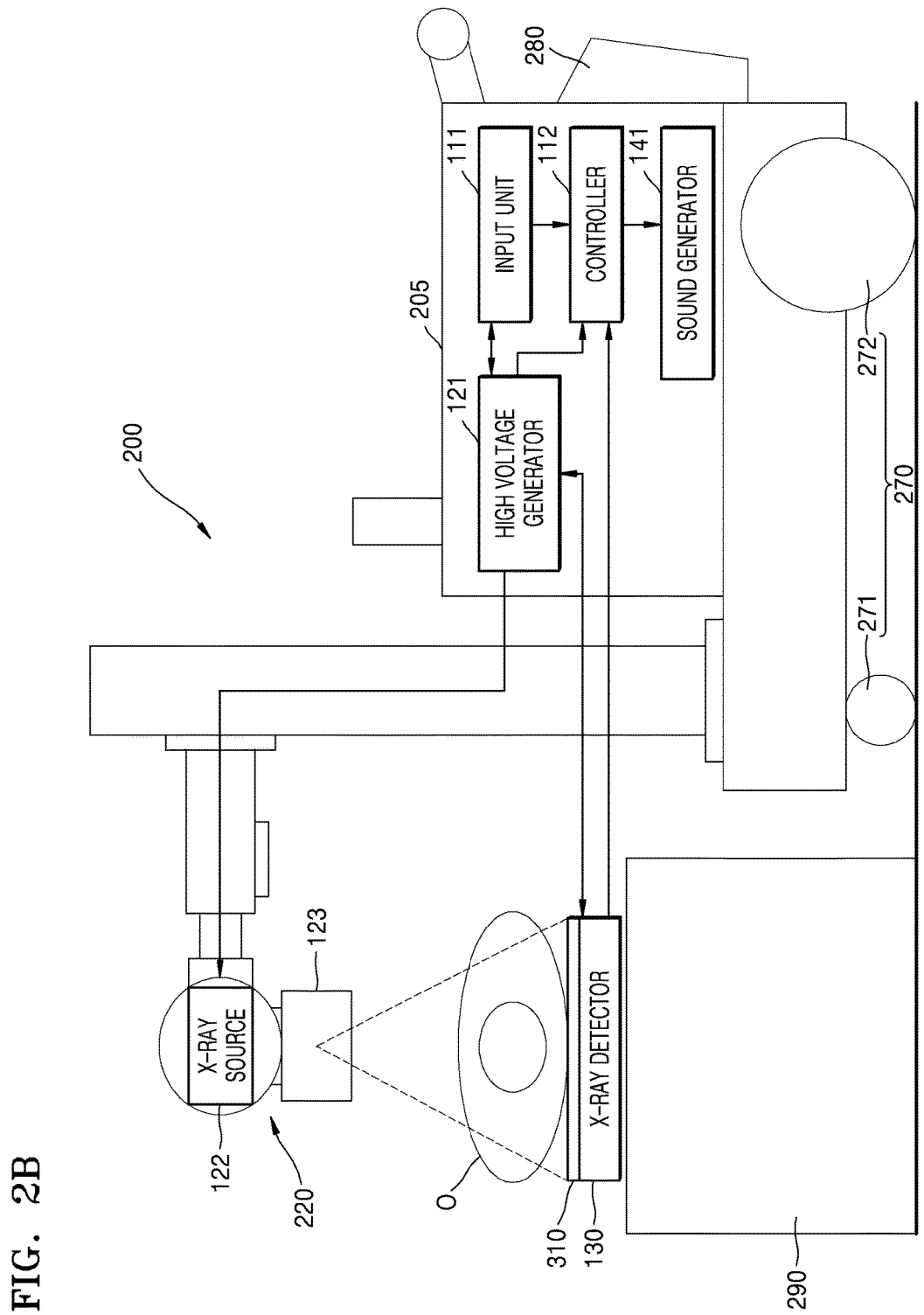
FIG. 2B is a schematic view illustrating an operational state of the X-ray apparatus according to an exemplary embodiment.

FIG. 2A is a schematic view illustrating an exemplary X-ray apparatus 200, and FIG. 2B is a schematic view illustrating an operational state of the X-ray apparatus 200 illustrated in FIG. 2A.

The X-ray apparatus 200 illustrated in FIGS. 2A and 2B is movable for taking X-ray images at any places.

The X-ray apparatus 200 includes an X-ray radiation unit 220 configured to emit X-rays to an object O; an X-ray detector 130 configured to detect X-rays passing through the object O; a guide unit 230 including a guide rail 231 to guide the X-ray radiation unit 220; a main body unit 205 supporting the guide unit 230 and including an input unit 111, a controller 112, a high voltage generator 121, and a sound generator 141; and a moving unit 270 including a plurality of wheels 271 and 272 for moving the main body unit 205.

The X-ray radiation unit 120 may include an X-ray source 122 configured to generate X-rays, and a collimator 123 configured to control a region on which X-rays emitted from the X-ray source 122 are incident.

The X-ray detector 130 detects X-rays passing through the object O. The X-ray detector 130 may include thin film transistors (TFTs) or charged coupled devices (CCDs).

The X-ray detector 130 may be placed at a particular place. For example, the X-ray detector 130 may be placed on a diagnostic table 290. After the object O is placed between the X-ray detector 130 and the X-ray radiation unit 220, the object O may be X-rayed. Instead of placing the X-ray detector 130 on the diagnostic table 290, the X-ray detector 130 may be placed at any other place as long as the X-ray detector 130 is disposed at a side of the object O opposite to the X-ray radiation unit 220.

When not used, the X-ray detector 130 may be placed in a storage pocket 280 provided on the main body unit 205.

When X-rays pass through the object O, some of the X-rays scatter in directions different from the incident direction of the X-rays (that is, scattering rays are generated). Such scattering rays increase in proportion to the thickness of the object O, and as scattering rays increase, the quality of X-ray images of the object O may deteriorate. Therefore, if the thickness of the object is 20 cm or greater (for example, if the object O is the chest of a patient), an X-ray grid 310 may be used to remove scattering rays by selectively transmitting X-rays.

However, if the object O is a hand or foot having a relatively small thickness, image quality is not largely lowered by scattering rays, and thus X-ray images having a certain degree of quality may be obtained without using the X-ray grid 310.

As described above, according to the object O to be X-rayed, an operator may determine whether to use the X-ray grid 310 together with the X-ray detector 130. To this end, the X-ray grid 310 may be configured to be easily detached from the X-ray detector 130.

Figure 3A:
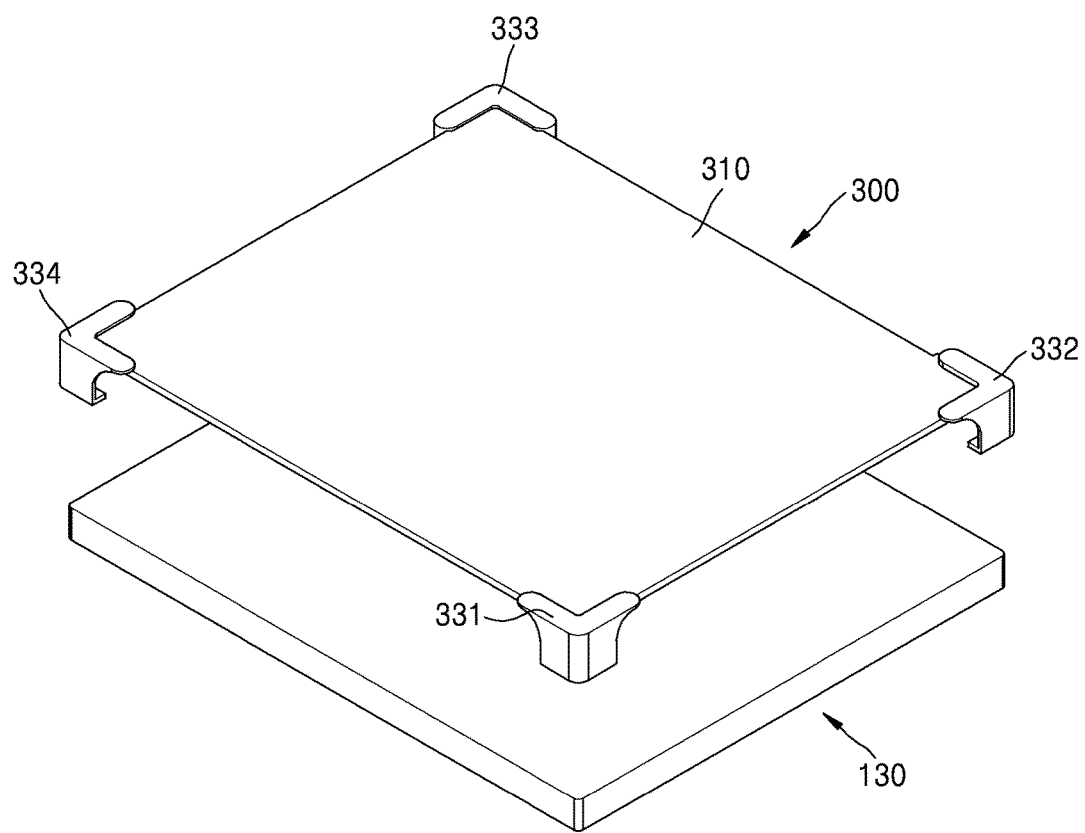
FIG. 3A is a perspective view illustrating the X-ray grid structure when separated from an X-ray detector according to an exemplary embodiment.
Figure 3B:
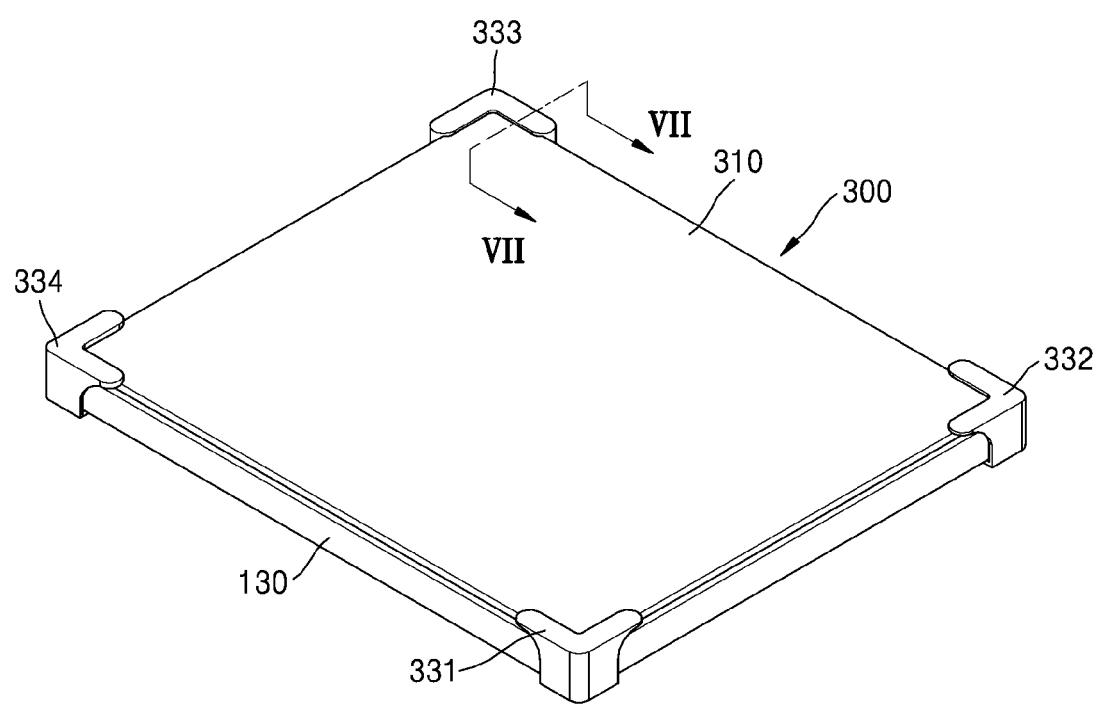
FIG. 3B is a perspective view illustrating the X-ray grid structure when attached to the X-ray detector 130 according to an exemplary embodiment.

FIGS. 3A and 3B illustrate an X-ray grid structure 300 according to one or more exemplary embodiments. FIG. 3A illustrates the X-ray grid structure 300 separated from the X-ray detector 130, and FIG. 3B illustrates the X-ray grid structure 300 attached to the X-ray detector 130. According to the thickness of an object O, an operator may use the X-ray detector 130 after separating the X-ray grid structure 300 from the X-ray detector 130 as shown in FIG. 3A or attaching the X-ray grid structure 300 to the X-ray detector 130 as shown in FIG. 3B.

Figure 4:
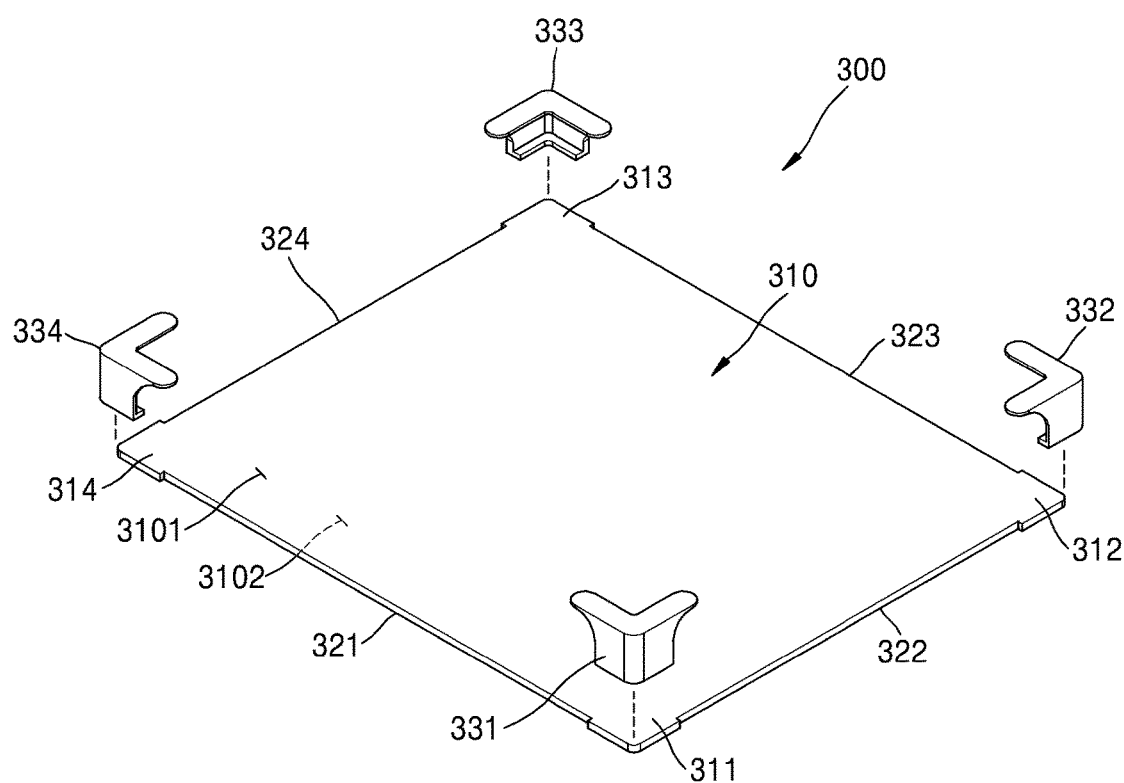
FIG. 4 is an exploded perspective view illustrating an X-ray grid structure, similar to the X-ray grid structure of FIG. 3A, according to an exemplary embodiment.
Figure 5:
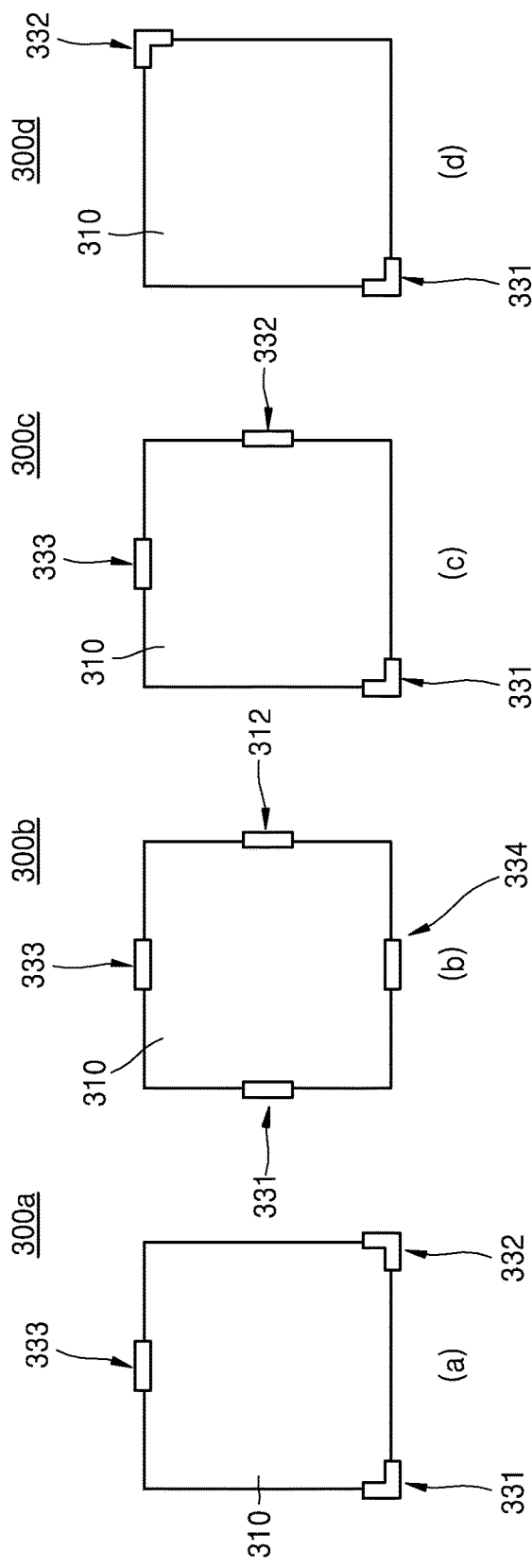
FIGS. 5A to 5D are views illustrating X-ray grid structures according to other exemplary embodiments of the present invention.

FIG. 4 is an exploded perspective view illustrating the X-ray grid structure 300 of FIG. 3A. Referring to FIG. 4, the X-ray grid structure 300 includes the X-ray grid 310, and a plurality of holders 331, 332, 333, and 334 used to detachably attach the X-ray grid 310 to the X-ray detector 130.

The X-ray grid 310 selectively transmits X-rays passing through an object O so that scattering rays generated when the X-rays passing through the object O may be filtered out. The X-ray grid 310 has a grating structure. The X-ray grid 310 may include an X-ray absorbing material. Examples of the X-ray absorbing material may include lead and tungsten.

The X-ray grid 310 may have a polygonal shape. For example, the X-ray grid 310 may have a rectangular shape as shown in FIG. 4. However, the shape of the X-ray grid 310 is not limited thereto. That is, the X-ray grid 310 may have any other shape such as a circular shape.

The X-ray grid 310 may include a rear side 3102 facing the X-ray detector 130 and a front side 3101 opposite to the rear side 3102. The X-ray grid 310 is positioned in such a manner that the front side 3101 faces an object O or the X-ray radiation unit 220 and the rear side 3102 faces the X-ray detector 130.

The plurality of holders 331, 332, 333, and 334 are fixed to the X-ray grid 310 and are used to detachably attach the X-ray grid 310 to the X-ray detector 130.

The holders 331, 332, 333, and 334 are fixed to portions of edges of the X-ray grid 310. The holders 331, 332, 333, and 334 are spaced apart from each other on the X-ray grid 310. For example, as shown in FIG. 4, four holders 331, 332, 333, and 334 may be disposed on corners 311, 312, 313, and 314 of the X-ray grid 310. However, the number and positions of the holders are not limited thereto. For example, as shown in FIGS. 5A to 5D, the number and positions of holders of X-ray grid structures 300a, 300b, 300c, and 300d may vary.

Because the holders 331, 332, 333, and 334 are arranged on portions of the edges of the X-ray grid 310 instead of being arranged along the entire edges of the X-ray grid 310, the weights of the holders 331, 332, 333, and 334 may be light. Therefore, an operator may experience less fatigue from lifting, connecting, and disconnecting which occur when using the X-ray grid structure 300. In other words, an operator may easily attach the X-ray grid structure 300 to the X-ray detector 130. As the X-ray grid structure 300 is frequently attached and detached, this effect may be increased.

When the X-ray grid structure 300 is attached to the X-ray detector 130, the holders 331, 332, 333, and 334 are pushed against the X-ray detector 130. At least one of the holders 331, 332, 333, and 334 pushed against the X-ray detector 130 may be bent in a direction crossing the attachment direction of the holders 331, 332, 333, and 334. This will be explained later in more detail with reference to FIGS. 9A to 9C.

To allow bending of the holders 331, 332, 333, and 334 when the holders 331, 332, 333, and 334 are pushed against the X-ray detector 130, the holders 331, 332, 333, and 334 may include an elastic material. The elastic material may include at least one of polyurethane and silicone.

Because the holders 331, 332, 333, and 334 include an elastic material, the holders 331, 332, 333, and 334 may be return to original shapes thereof after a pushing force is removed. In this manner, the X-ray grid structure 300 may be attached to the X-ray detector 130.

Furthermore, because the holders 331, 332, 333, and 334 include an elastic material, the X-ray detector 130 may not be damaged by contact or friction with the X-ray grid structure 300 when the X-ray grid structure 300 is attached to the X-ray detector 130. If the holders 331, 332, 333, and 334 are formed of a hard material such as metal, the X-ray detector 130 may be scratched by friction or collision with the holders 331, 332, 333, and 334.

According to one or more exemplary embodiments, the holders 331, 332, 333, and 334 may have a Shore A hardness of about 70 to about 95 i.e., as measured by a type A Shore Durometer. If the Shore A hardness of the holders 331, 332, 333, and 334 is less than about 70, the holders 331, 332, 333, and 334 may be unintentionally bent. For example, when the X-ray detector 130 to which the X-ray grid structure 300 is attached is moved, the holders 331, 332, 333, and 334 may not resist the weight of the X-ray detector 130 and may be bent. In this case, the X-ray detector 130 may be separated from the holders 331, 332, 333, and 334. On the other hand, if the Shore A hardness of the holders 331, 332, 333, and 334 is greater than about 95, the holders 331, 332, 333, and 334 may not be bent when pushed against the X-ray detector 130. In this case, the X-ray detector 130 may not be held by the holders 331, 332, 333, and 334.

The holders 331, 332, 333, and 334 may have the same shape and formed of the same material. In this case, the holders 331, 332, 333, and 334 may be manufactured with high productivity.

Figure 6:
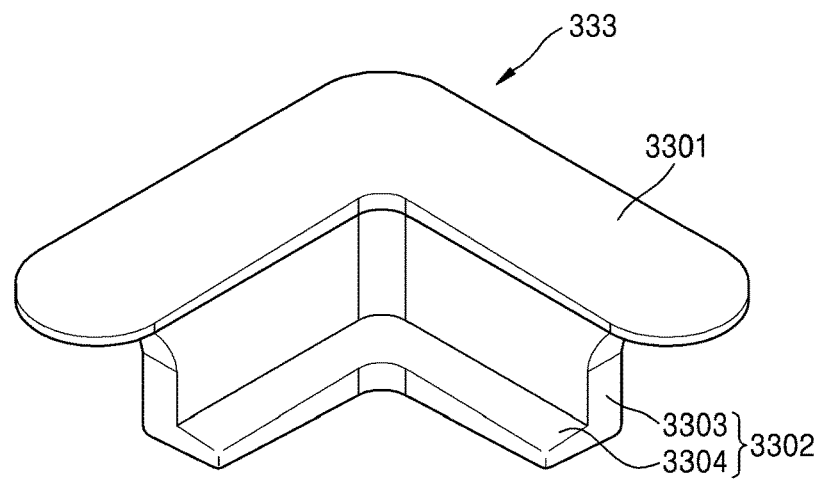
FIG. 6 is an enlarged perspective view illustrating a holder of a plurality of holders according to an exemplary embodiment.
Figure 7:
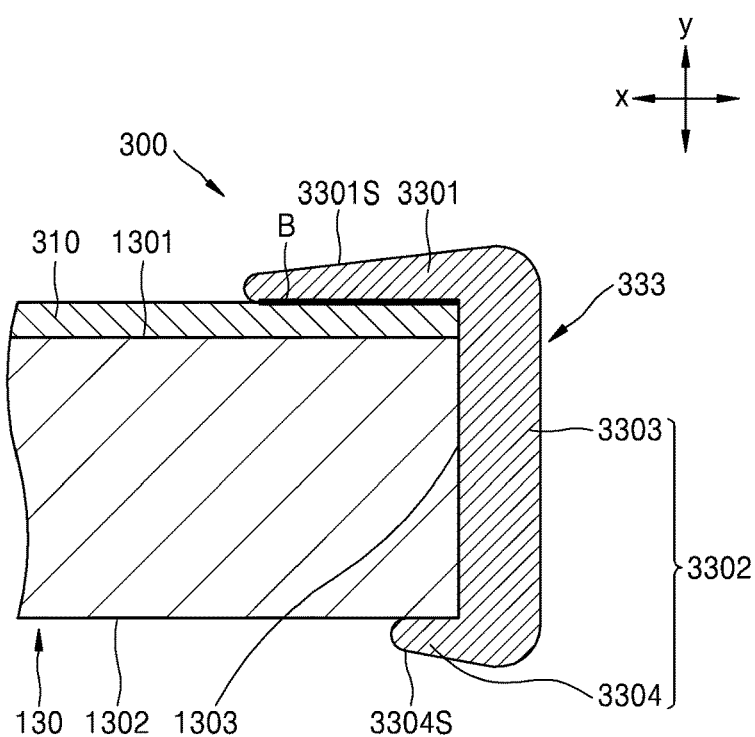
FIG. 7 is a cross-sectional view taken along line VI-VI of FIG. 3B according to an exemplary embodiment.

FIG. 6 is an enlarged perspective view illustrating one of the holders 331, 332, 333, and 334, and FIG. 7 is a sectional view taken along line VI-VI of FIG. 3B. Although FIG. 6 illustrates the (third) holder 333, the other holders 331, 332, and 334 may have the same shape as the holder 333 shown in FIG. 6.

Referring to FIGS. 6 and 7, the holder 333 includes a fixing portion 3301 fixed to the X-ray grid 310, and a support portion 3302 extending from the fixing portion 3301 and supporting the X-ray detector 130.

The fixing portion 3301 may extend in a surface direction (x-axis direction) of the X-ray grid 310. The fixing portion 3301 may be fixed to portions of edges of the X-ray grid 310. The fixing portion 3301 may be fixed to the X-ray grid 310 using an adhesive. By using an adhesive, the holder 333 may be stably fixed to the X-ray grid 310 without increasing a thickness of the holder 333 and the X-ray grid 310. In addition, the holder 333 may be stably fixed to the X-ray grid 310 without damaging or breaking the X-ray grid 310. The X-ray grid 310 may have a thickness of about 1 mm to about 2 mm. The thickness of the X-ray grid 310 is measured in a y-axis direction perpendicular to the x-axis direction.

If the fixing portion 3301 is fixed to the X-ray grid 310 by other methods such as a screw coupling method, the holder 333 or the X-ray grid 310 may have to be thick, or the holder 333 may not be stably fixed to the X-ray grid 310. Furthermore, if the holder 333 is fixed to the X-ray grid 310 using a screw, when the holder 333 is bent, stress may be concentrated on a region of the X-ray grid 310 because of the screw, and thus the X-ray grid 310 may be broken.

However, if the fixing portion 3301 is fixed to the X-ray grid 310 through an adhesive B which is widely applied, when the holder 333 is bent, stress may not be concentrated on a region of the X-ray grid 310, and thus the X-ray grid 310 may not be broken. For example, the adhesive B may be an epoxy-containing resin.

The support portion 3302 may include a side support portion 3303 extending from the fixing portion 3301 in the y-axis direction perpendicular to the surface direction (x-axis direction) of the X-ray grid 310; and a rear support portion 3304 extending from the side support portion 3303 in the surface direction (x-axis direction) of the X-ray grid 310.

The X-ray detector 130 includes a front side 1301 facing the X-ray grid 310, a rear side 1302 opposite to the front side 1301, and a lateral side 1303 between the front side 1301 and the rear side 1302. After the X-ray grid structure 300 is attached to the X-ray detector 130, the side support portion 3303 supports the lateral side 1303 of the X-ray detector 130, and the rear support portion 3304 supports the rear side 1302 of the X-ray detector 130.

When the X-ray grid structure 300 is attached to the X-ray detector 130, the support portion 3302 may be pushed by the X-ray detector 130 and thus may be bent. If the pushing force applied to the support portion 3302 from the X-ray detector 130 is removed, the support portion 3302 may return to the original shape thereof.

Figure 8A:
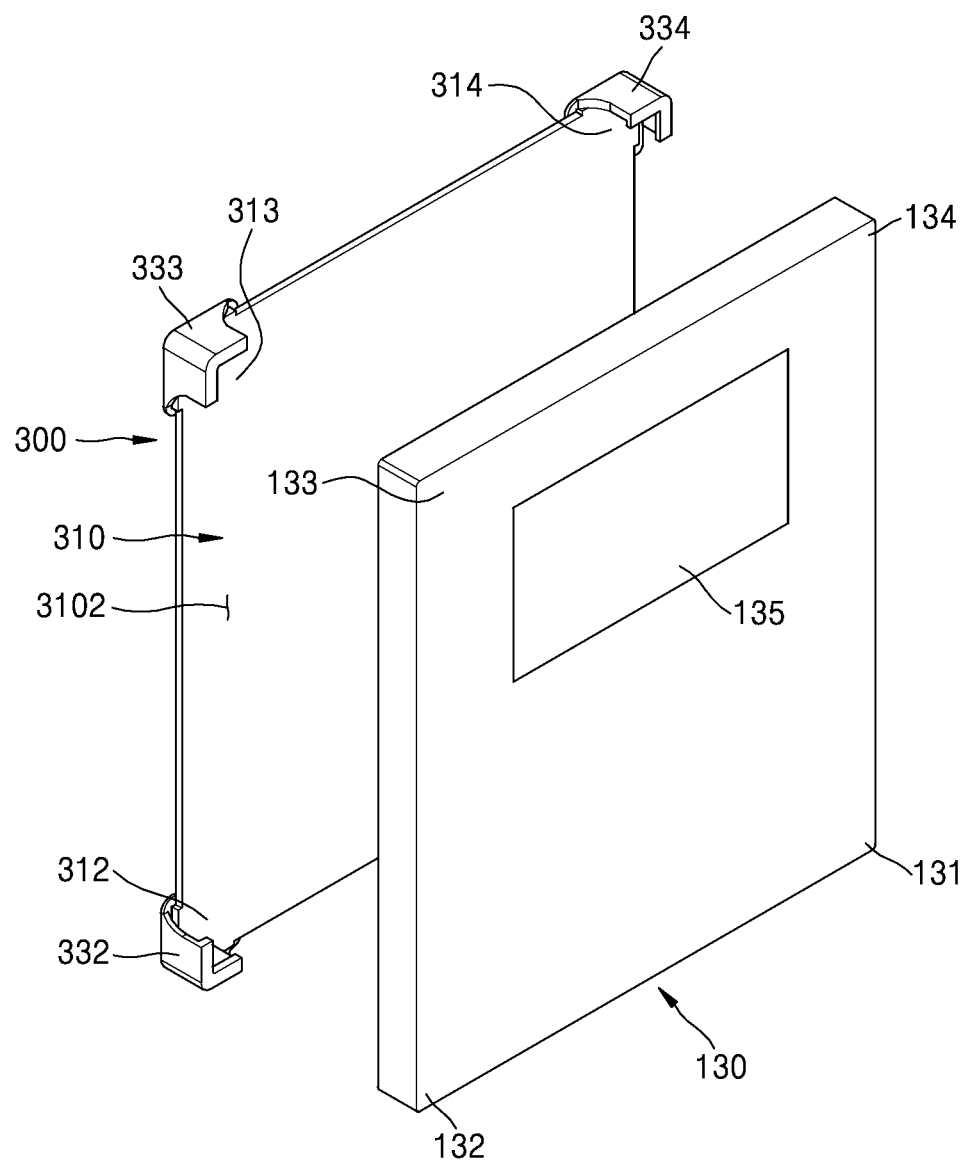
FIGS. 8A, 8B, and 8C are views sequentially illustrating a process of attaching an X-ray detector to an X-ray grid structure according to an exemplary embodiment.
Figure 8B:
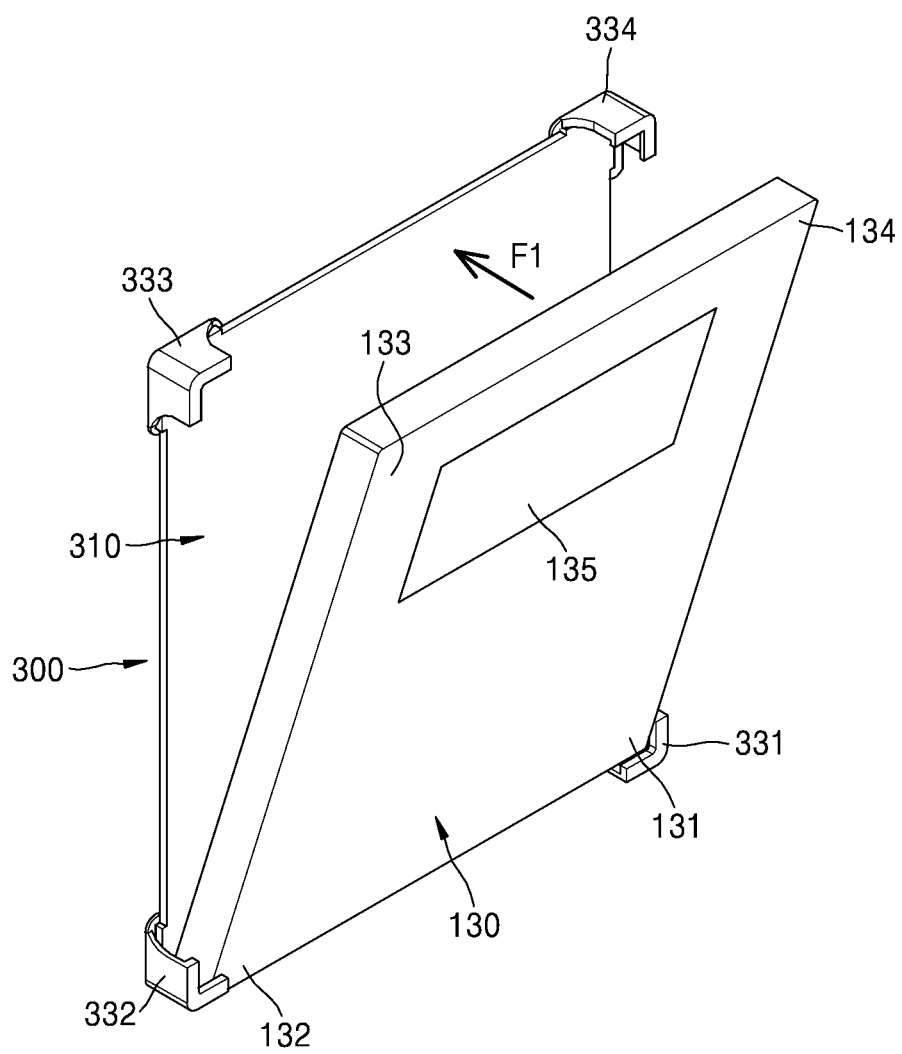
Figure 8C:
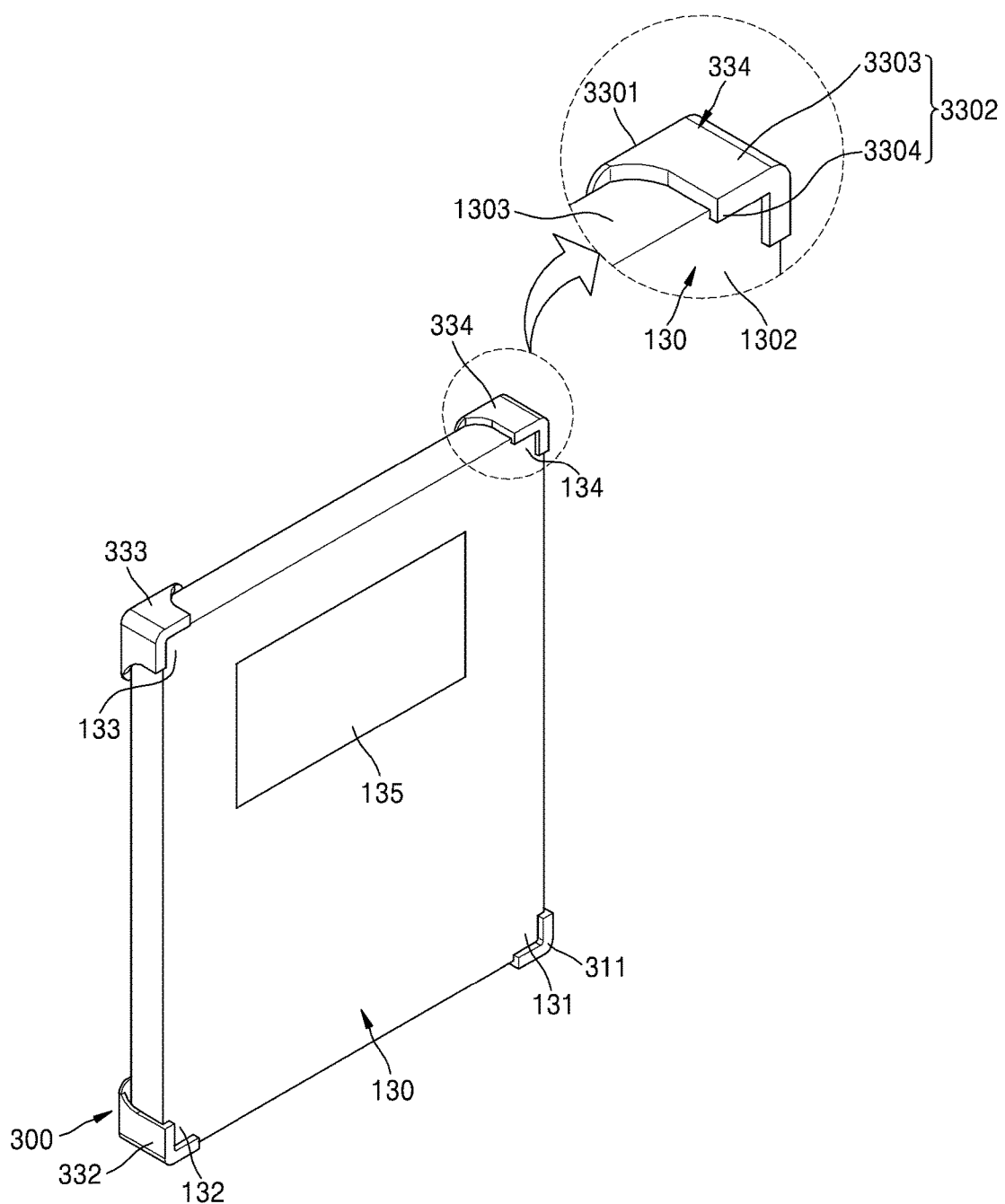
Figure 9A:
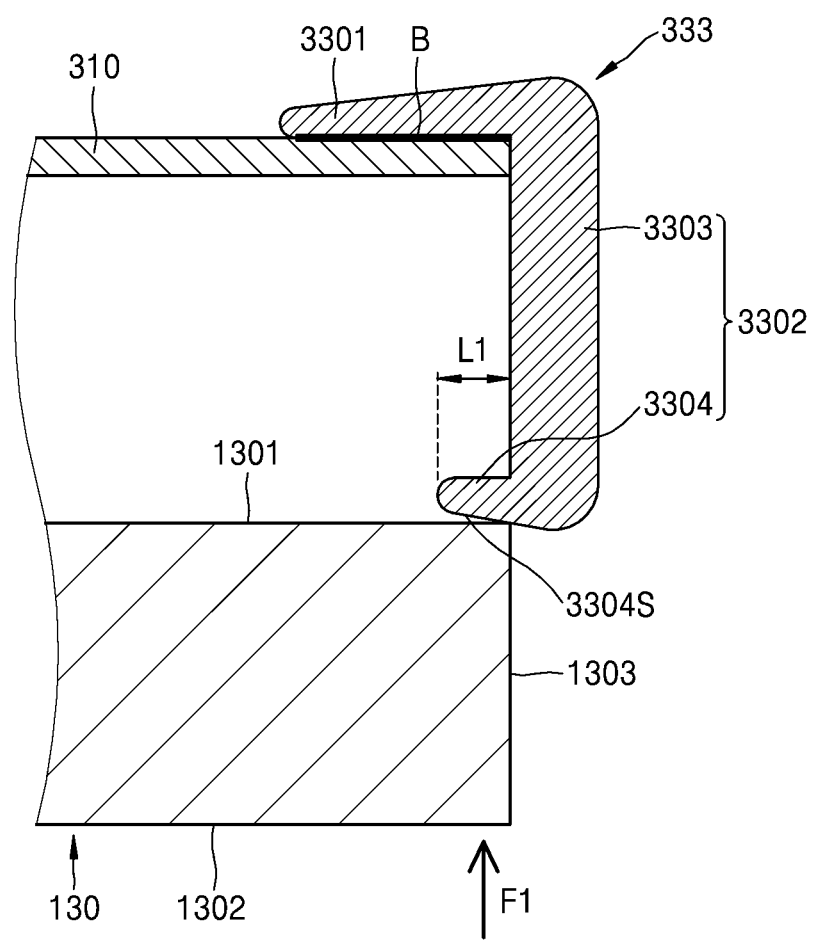
FIGS. 9A, 9B, and 9C are views illustrating an attachment process of an X-ray detector based on a shape change of a holder according to an exemplary embodiment.
Figure 9B:
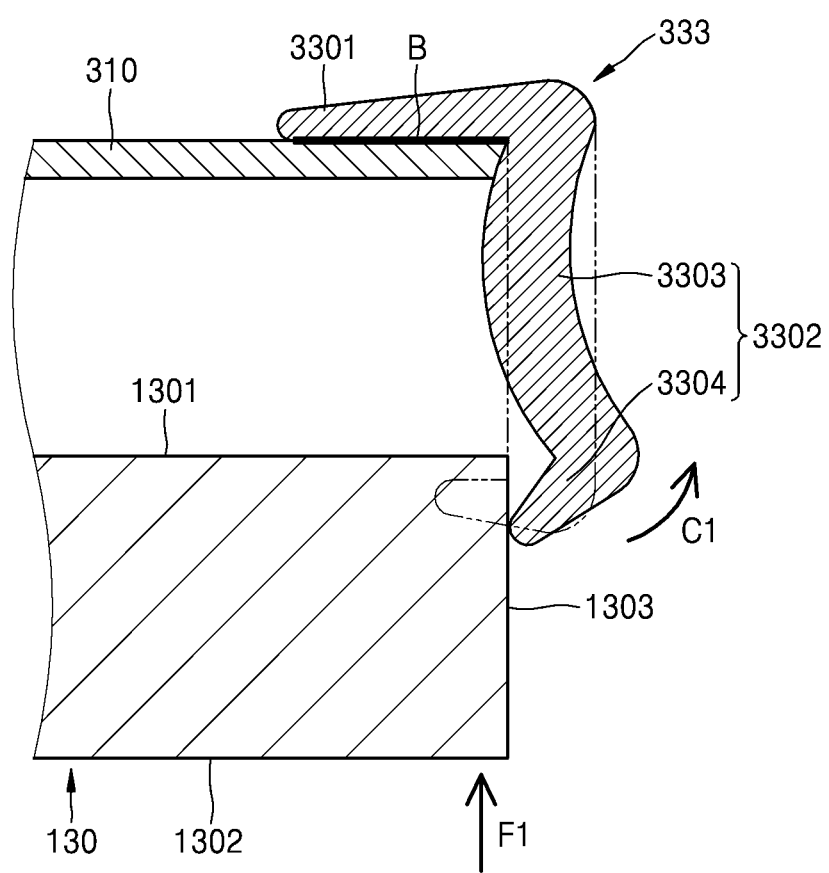
Figure 9C:
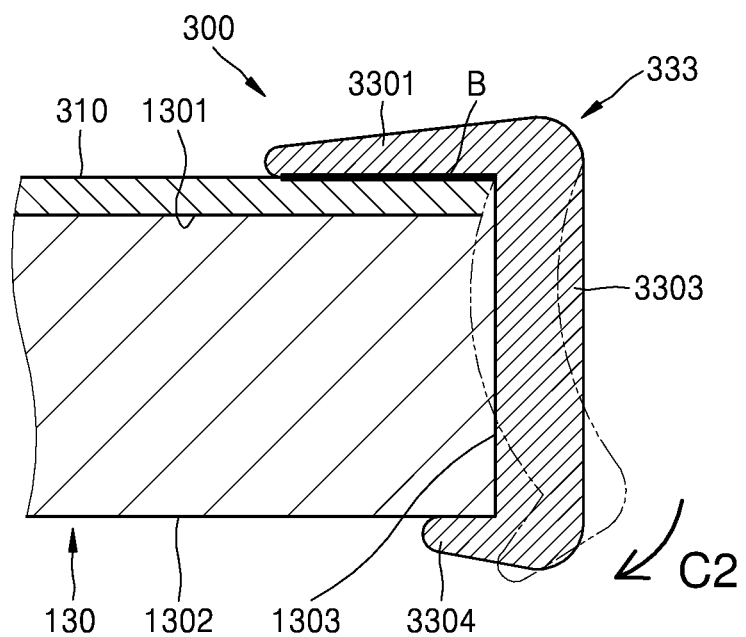

FIGS. 8A to 8C are views sequentially illustrating a process of attaching the X-ray detector 130 shown in FIG. 3A to the X-ray grid structure 300. FIGS. 9A to 9C are views illustrating the attachment process of the X-ray detector 130 of FIG. 3A based on the shape change of the holder 333. The method of attaching the X-ray grid structure 300 to the X-ray detector 130 is similar to the method of attaching the X-ray detector 130 to the X-ray grid structure 300, and thus will not be repeatedly described.

Referring to FIG. 8A, the X-ray detector 130 and the X-ray grid structure 300 are prepared. The function of the X-ray detector 130 is to detect X-rays emitted from the X-ray radiation unit 120 and passing through an object O. A battery may be attached to the X-ray detector 130 through a cover 135. The X-ray grid structure 300 includes the X-ray grid 310, and the plurality of holders 331, 332, 333, and 334 (e.g., first to fourth holders 331, 332, 333, and 334) fixed to the corners of the X-ray grid 310.

Referring to FIG. 8B, a first corner 131 and a second corner 132 of the X-ray detector 130 are inserted into the first and second holders 331 and 332. In this state, the X-ray detector 130 is moved so that a third corner 133 and a fourth corner 134 of the X-ray detector 130 may approach the third and fourth holders 333 and 334. Then, the third and fourth corners 133 and 134 of the X-ray detector 130 are brought into contact with the third and fourth holders 333 and 334. In this state, if the X-ray detector 130 is pushed toward the X-ray grid 310 in an attachment direction F1, the holders 331, 332, 333, and 334 are bent in directions crossing the attachment direction F1, and the X-ray detector 130 is attached to the X-ray grid structure 300.

Referring to FIG. 8C, after the X-ray detector 130 is attached to the X-ray grid structure 300, the lateral side 1303 of the X-ray detector 130 is supported by the side support portions 3303 of the holders 331, 332, 333, and 334, and the rear side 1302 of the X-ray detector 130 is supported by the rear support portions 3304 of the holders 331, 332, 333, and 334.

With reference to FIGS. 9A to 9C, an explanation will now be given of the change of the holder 333 when the X-ray detector 130 is attached to the X-ray grid structure 300.

Referring to FIG. 9A, as the X-ray detector 130 is moved toward the X-ray grid 310, the front side 1301 of the X-ray detector 130 is brought into contact with the rear support portion 3304 of the holder 333.

Referring to FIG. 9B, as the X-ray detector 130 is pushed toward the X-ray grid 310 in the attachment direction F1, the support portion 3302 is bent in a direction C1 crossing the attachment direction F1. The X-ray detector 130 is pushed in the attachment direction F1 in a state in which the lateral side 1303 of the X-ray detector 130 makes contact with the rear support portion 3304.

Referring to FIG. 9C, as the X-ray detector 130 is further pushed, the X-ray detector 130 is moved closer to the X-ray grid 310, and the contact of the lateral side 1303 of the X-ray detector 130 and the rear support portion 3304 ends. As a result, a pushing force applied from the X-ray detector 130 to the rear support portion 3304 is removed, and the rear support portion 3304 returns (in a direction C2) to an original position thereof. Then, the rear support portion 3304 supports the rear side 1302 of the X-ray detector 130, and the side support portion 3303 supports the lateral side 1303 of the X-ray detector 130. In this way, the attachment of the X-ray detector 130 to the X-ray grid structure 300 is completed as shown in FIG. 8C.

Referring again to FIG. 9A, the rear support portion 3304 may have a length L1 of about 3 mm to about 6 mm. If the length L1 of the rear support portion 3304 is smaller than about 3 mm, the rear support portion 3304 may not sufficiently support the X-ray detector 130. On the other hand, if the length L1 of the rear support portion 3304 is greater than about 6 mm, when the X-ray detector 130 is attached, the end of the rear support portion 3304 may be bent in the attachment direction F1 of the X-ray detector 130 and may be inserted between the lateral side 1303 of the X-ray detector 130 and the side support portion 3303.

The rear support portion 3304 may have a slope 3304S having an outwardly increasing height. When the rear support portion 3304 is brought into contact with the X-ray detector 130 and pushed by the X-ray detector 130, the slope 3304S of the rear support portion 3304 makes contact with the X-ray detector 130 so that the rear support portion 3304 may be smoothly moved in the direction C1 while being pushed by the X-ray detector 130.

In the above-described embodiments, the holders 331, 332, 333, and 334 are fixed to the X-ray grid structure 310 by using the adhesive B. However, the holders 331, 332, 333, and 334 may be fixed to the X-ray grid structure 310 by using another method.

Figure 10:
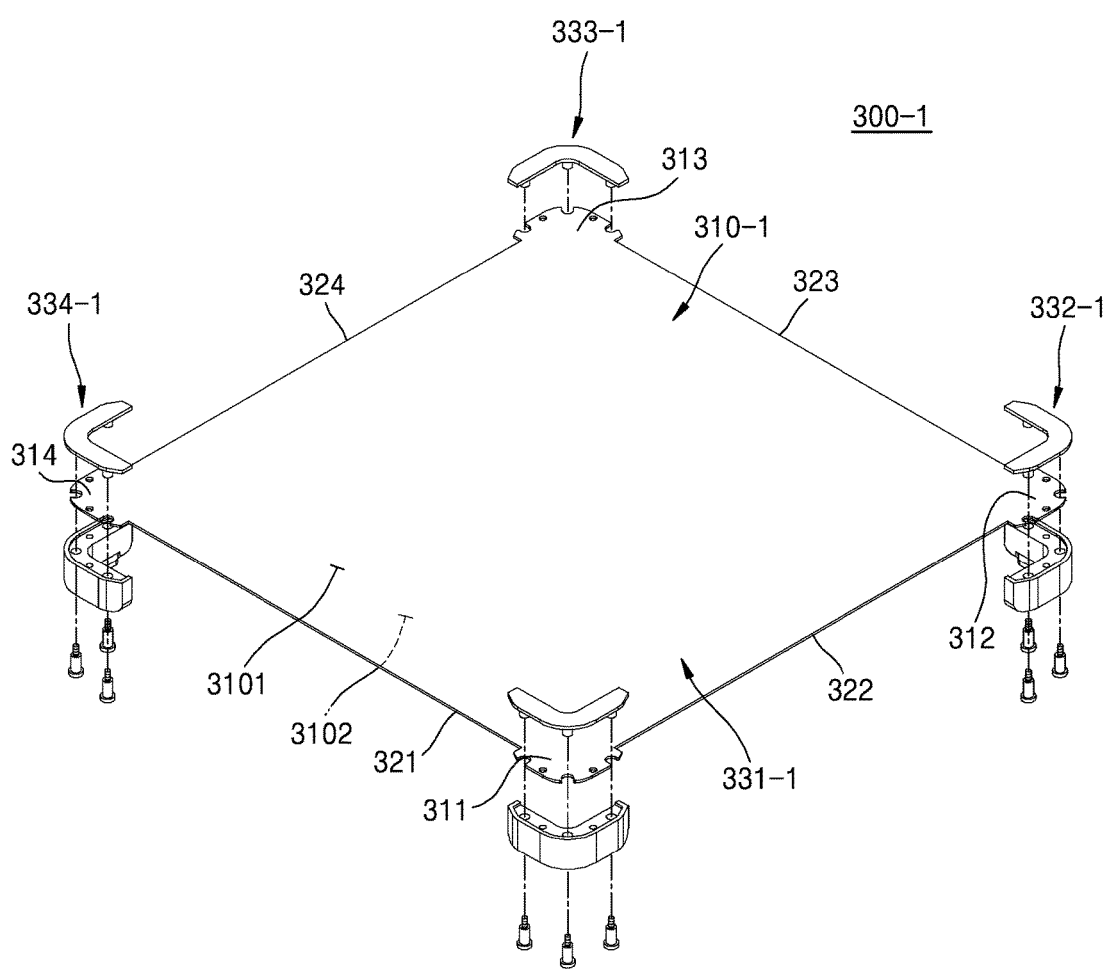
FIG. 10 is an exploded perspective view illustrating a modified example of the X-ray grid structure of FIG. 3A, according to another exemplary embodiment.
Figure 11A:
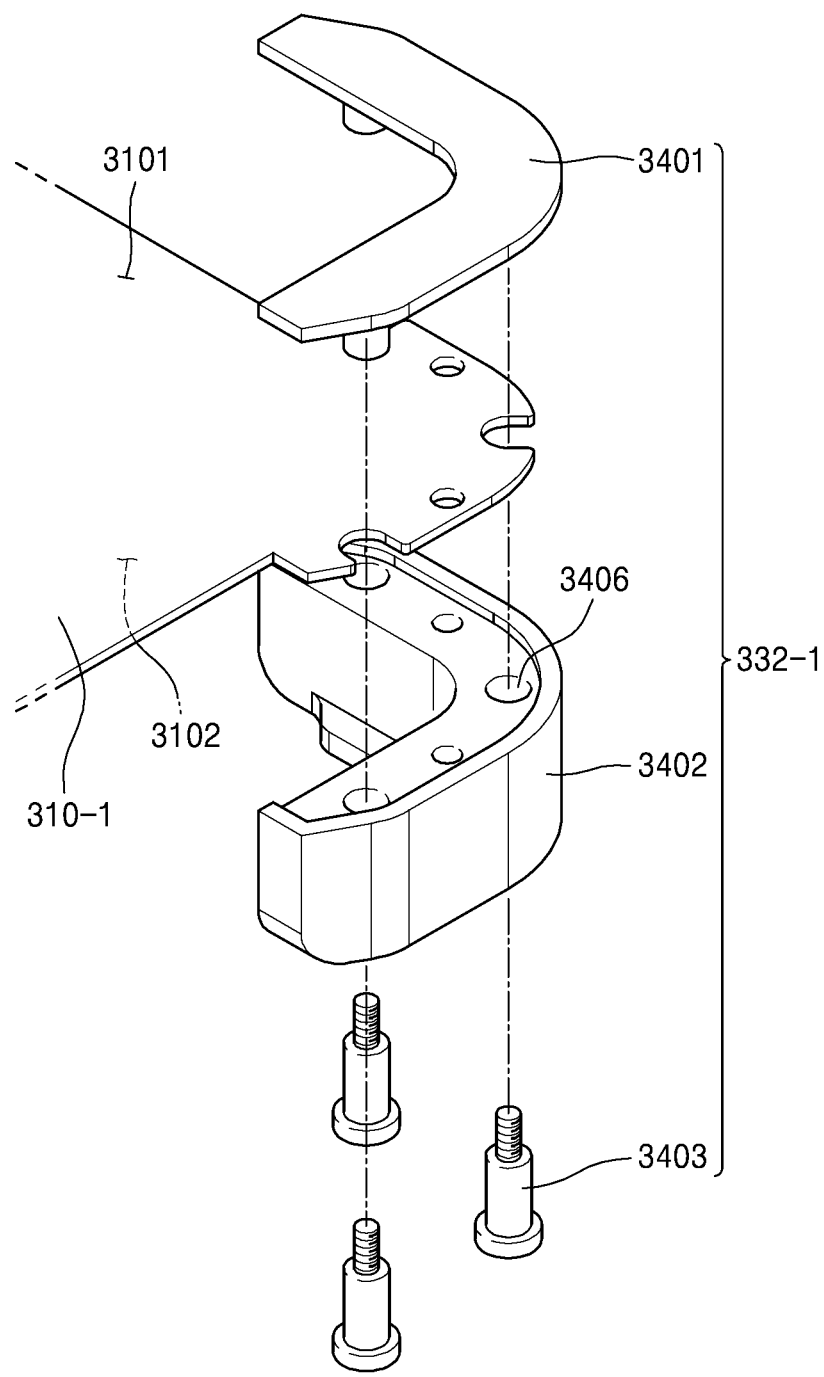
FIG. 11A is an enlarged view of a portion illustrated in FIG. 10.

FIG. 10 is an exploded perspective view illustrating a modified example of the X-ray grid structure of FIG. 3A, according to another exemplary embodiment. FIG. 11A is an enlarged view of a portion illustrated in FIG. 10, and FIG. 11B is a view of the portion from a different angle.

Referring to FIG. 10, an X-ray grid structure 300-1 includes an X-ray grid 310-1, and a plurality of holders 331-1, 332-1, 333-1, and 334-1 used to detachably attach the X-ray grid 310-1 to the X-ray detector 130.

The same description as that given in the previous exemplary embodiments will not be repeated, and differences will be mainly described below.

Figure 11B:
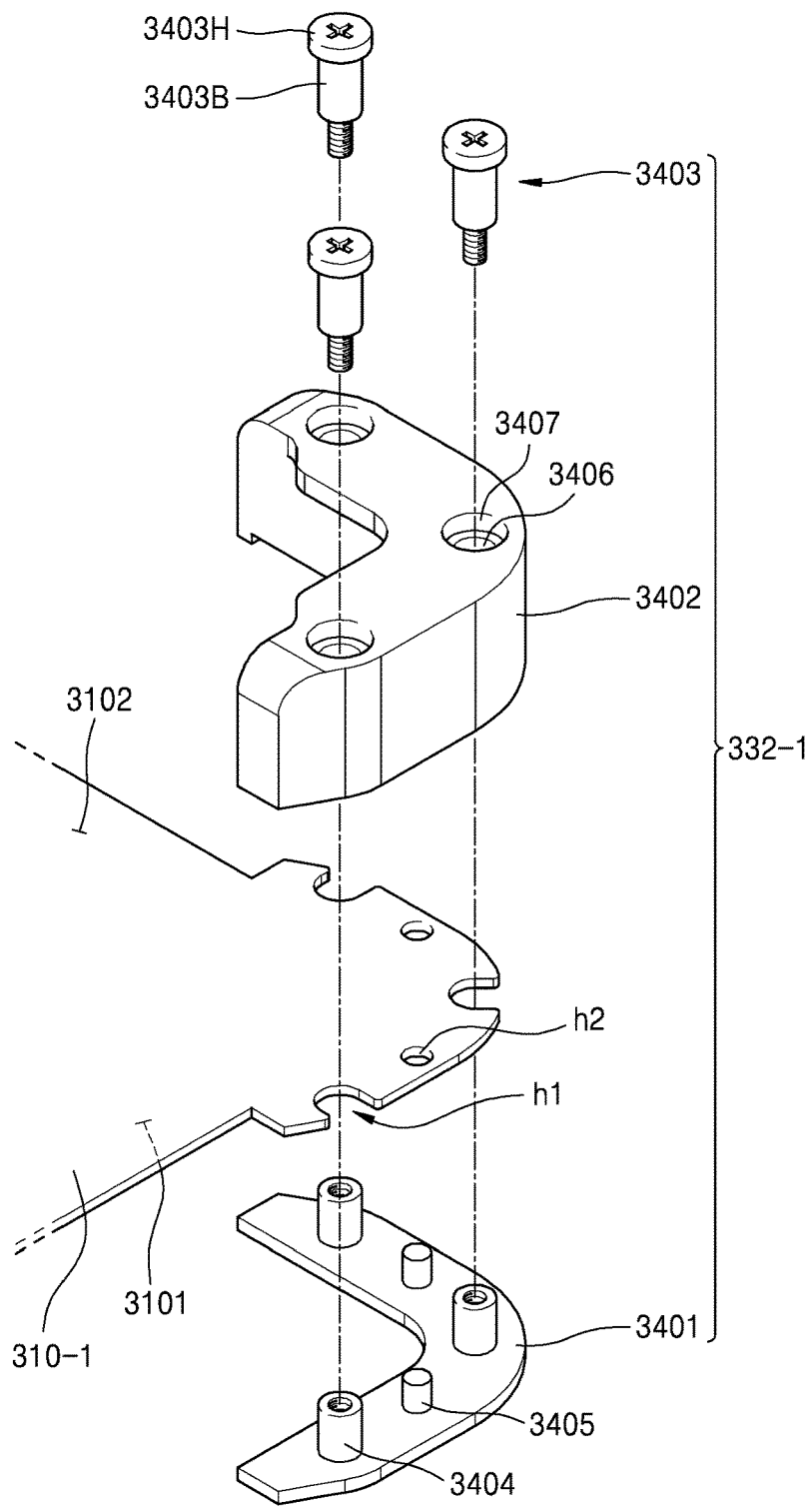
FIG. 11B is a view of the portion from a different angle.

Referring to FIGS. 11A and 11B, each of the holders 331-1, 332-1, 333-1, and 334-1 includes a first member 3401 contacting a rear side 3101 of the X-ray grid 310-1, a second member 3402 contacting a front side 3102 of the X-ray grid 310-1, and coupling members 3403 fastening the first member 3401 and the second member 3402. Hereinafter, the holder 332-1 of the holders 331-1, 332-1, 333-1, and 334-1 will be mainly described for clarity of illustration.

The first member 3401 includes a plurality of coupling hole structures 3404 for coupling with the coupling members 3403. The coupling hole structures 3404 protrude toward the second member 3402. The first member 3401 may further include guide protrusions 3405 for determining the positions of the second member 3402. The guide protrusions 3405 may be arranged between the coupling hole structures 3404. The X-ray grid 310-1 may include openings h1 and h2 for receiving the coupling hole structures 3404 and the guide protrusions 3405 of the first member 3401.

The coupling members 3403 include body portions 3403B for coupling with the coupling hole structures 3404 of the first member 3401, and head portions 3403H for pressing the second member 3402. Diameters of the head portions 3403H are greater than diameters of the body portions 3403B.

The second member 3402 includes connection holes 3406 which receive the coupling members 3403 and are connected to the coupling hole structures 3404 of the first member 3401. The connection holes 3406 include support grooves 3407 to support the head portions 3403H of the coupling members 3403.

Figure 12A:
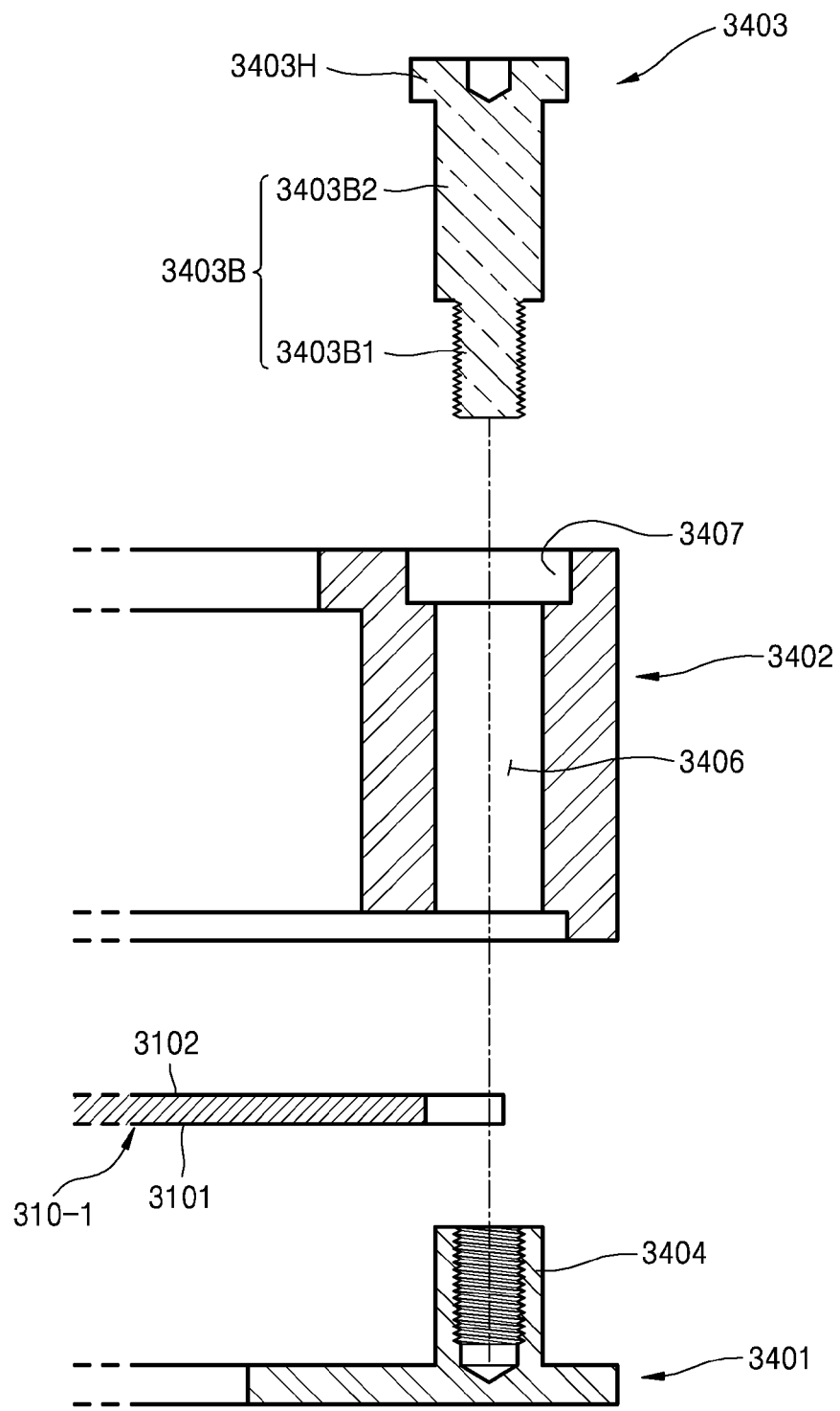
FIG. 12A is a cross-sectional view of the portion of FIG. 11B.
Figure 12B:
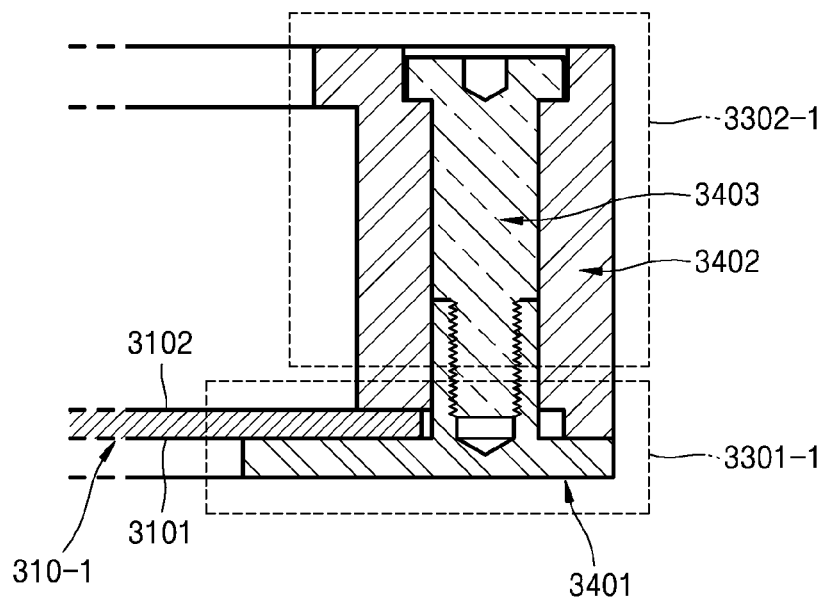
FIG. 12B is a cross-sectional view illustrating a state in which first and second members of a holder illustrated in FIG. 12A are coupled to each other using coupling members and thus the holder is fixed to an X-ray grid.

FIG. 12A is a cross-sectional view of the portion illustrated in FIG. 11B, and FIG. 12B is a cross-sectional view illustrating a state in which the first and second members 3401 and 3402 of the holder 332-1 illustrated in FIG. 12A are coupled to each other using the coupling members 3403 and thus the holder 332-1 is fixed to the X-ray grid 310-1.

Referring to FIGS. 12A and 12B, the first member 3401 of the holder 332-1 supports the rear side 3101 of the X-ray grid 310-1, and the second member 3402 of the holder 332-1 supports the front side 3102 of the X-ray grid 310-1. In this state, if the coupling members 3403 are coupled, the X-ray grid 310-1 is pressed by the first member 3401 and the second member 3402. In this way, the holder 332-1 is fixed to the X-ray grid 310-1.

The first member 3401 and a portion of the second member 3402 may correspond to the fixing portion 3301 described in the previous embodiments, and a remaining portion of the second member 3402 may correspond to the support portion 3302 described in the previous exemplary embodiments.

The body portions 3403B of the coupling members 3403 include threaded regions 3403B1 inserted into the coupling hole structures 3404 and screwed to the coupling hole structures 3404. When the threaded regions 3403B1 of the coupling members 3403 are moved toward the first member 3401 while being screwed to the coupling hole structures 3404, the second member 3402 is pressed at the support grooves 3407 by the heads 3402H of the coupling members 3403.

The body portions 3403B of the coupling members 3403 may include non-threaded regions 3403B2 on which threads are not formed. When the coupling members 3403 are coupled, the coupling members 3403 are not screwed to the connection holes 3406 of the second member 3402. Therefore, the second member 3402 may not be deteriorated by heat generated during screw coupling and may not be deformed by pressure applied from the coupling members 3403 during screw coupling.

At least a portion of the second member 3402 may include an elastic material so as to be bent when being pressed by the X-ray detector 130. The elastic material may include one or more of polyurethane and silicone.

Figure 13:
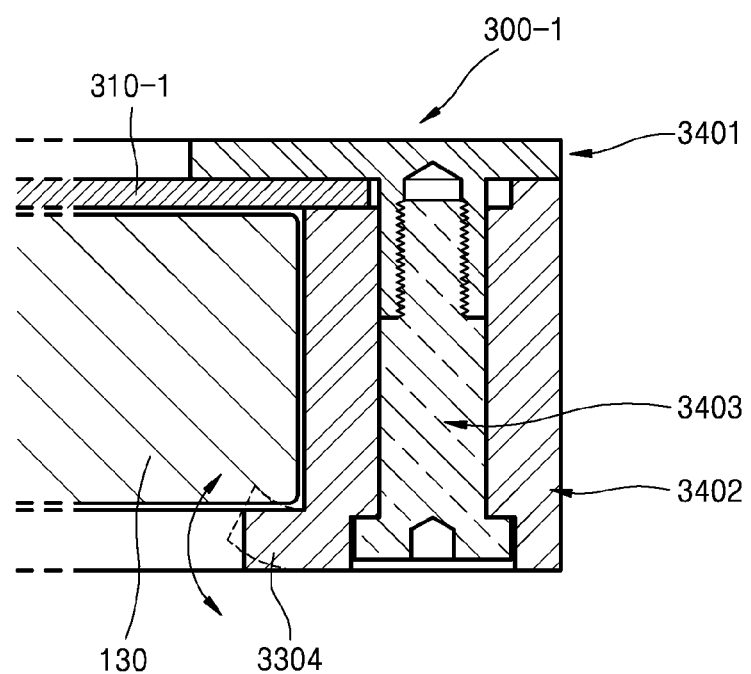
FIG. 13 is a view illustrating a state in which an X-ray detection unit is attached to the X-ray grid structure.

FIG. 13 is a view illustrating a state in which the X-ray detector 130 is attached to the X-ray grid structure 300-1. Referring to FIG. 13, when the X-ray detector 130 is moved close to the X-ray grid 310-1 of the X-ray grid structure 300-1, a portion 3304 of the second member 3402 may be elastically deformed, and then the X-ray detector 130 may be attached to the X-ray grid structure 300-1.

Referring back to FIG. 12A, the first member 3401 may include a material that is different from a material included in the second member 3402. For example, the first member 3401 may have a bending strength greater than that of the second member 3402. The bending strength may be considered as an elastic deformation force. It may be relatively difficult to elastically deform the first member 3401 compared to the case of elastically deforming the second member 3402. In this case, the first member 3401 may be easily coupled to the coupling members 3403. For example, the first member 3401 may include a plastic material or a metallic material as a material having a bending strength greater than that of the second member 3402. Examples of the plastic material may include polycarbonate, an acrylonitrile-butadiene-styrene (ABS) resin, and polyethylene. Examples of the metallic material may include stainless steels (STSs), carbon steels for mechanical structures, aluminum alloys, and cold-rolled steels (SPCC). Examples of the carbon steels for mechanical structures may include SM45C and SM25C specified in Korean Industrial Standards (KS), and examples of the aluminum alloys may include AL6061 and AL6064 specified in KS. The first member 3401 may make contact with an object O to be X-rayed. Since the first member 3401 includes a plastic material or a metallic material, friction between the first member 3401 and the object O may be relatively low when compared to friction between an elastic material and the object O. Therefore, the object O may experience less inconvenience.

In the previous embodiments, it is described that all of the holders 331-1, 332-1, 333-1, and 334-1 are plastically deformable. However, the holders 331-1, 332-1, 333-1, and 334-1 are not limited thereto. For example, some of the holders 331-1, 332-1, 333-1, and 334-1 may be rigid bodies that are not elastically deformable.

Figure 14:
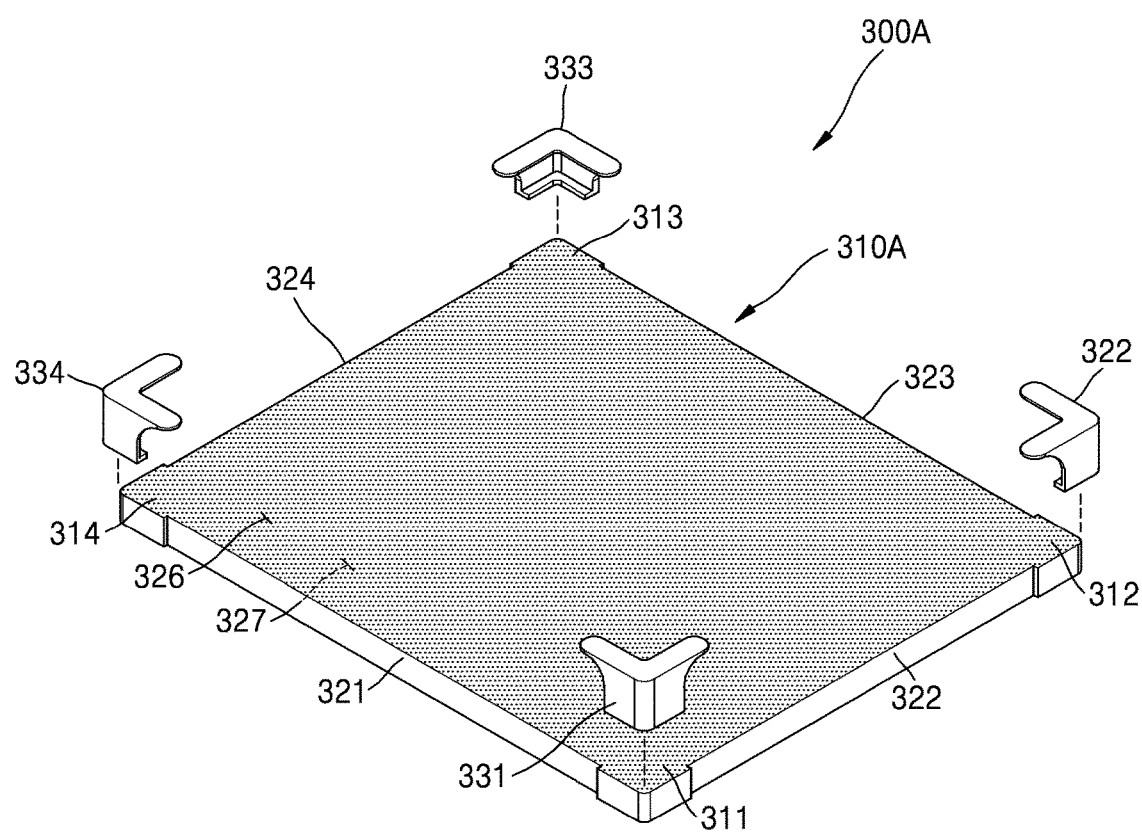
FIG. 14 illustrates an X-ray grid structure as a modified version of an X-ray grid structure, according to another embodiment.

FIG. 14 illustrates an X-ray grid structure 300A according to another exemplary embodiment. The X-ray grid structure 300A shown in FIG. 14 is constructed by attaching reinforcement films 326 and 327 to the X-ray grid 310 shown in FIG. 4, and other structures of the X-ray grid structure 300A are the same as those of the X-ray grid structure 300 shown in FIG. 4. Thus, descriptions of the same structures will not be repeated, and the following description of the X-ray grid structure 300A will be focused on different structures.

The reinforcement films 326 and 327 may be disposed on the front side and rear side of an X-ray grid 310A. The reinforcement films 326 and 327 may reinforce the X-ray grid 310A and the X-ray grid structure 300A. In the X-ray grid structure 300A of the current exemplary embodiment, because the X-ray grid 310A is not reinforced by holders 331, 332, 333, and 334, the reinforcement films 326 and 327 may be used to protect the X-ray grid 310A. Because the reinforcement films 326 and 327 are disposed on the front and rear sides of the X-ray grid 310A, the X-ray grid 310A may not be broken even though the X-ray grid 310A is bent in any direction when being attached to or detached from the X-ray detector 130.

The reinforcement films 326 and 327 may be formed of carbon fiber. Because carbon fiber has a high x-ray transmittance, the x-ray transmittance of the X-ray grid 310A may not be lowered by the reinforcement films 326 and 327.

Referring FIG. 7, the fixing portion 3301 may include a slope 3301S having a height increasing in an outward direction of the X-ray grid 310.

Figure 15:
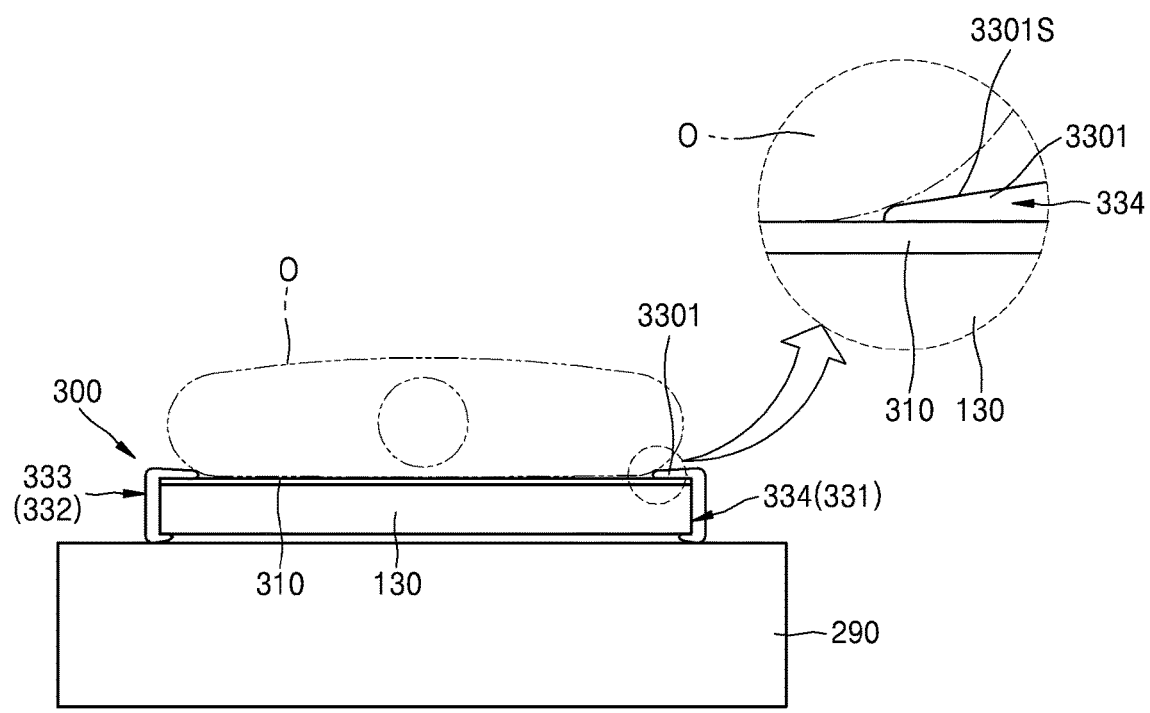
FIG. 15 is a schematic view including an arrangement in which an X-ray detector to which an X-ray grid structure is attached is placed on a diagnostic table according to an exemplary embodiment.

FIG. 15 schematically illustrates an arrangement in which the X-ray detector 130 coupled with the X-ray grid structure 300 is disposed on the diagnostic table 290 so as to explain the function of the slope 3301S of the fixing portion 3301.

Referring to FIG. 15, the X-ray detector 130 to which the X-ray grid structure 300 is attached is positioned so that the X-ray grid 310 faces an object O. In this arrangement, X-rays passing through the object O are incident on the X-ray detector 130 through the X-ray grid 310.

The object O is on the X-ray grid structure 300, and the fixing portions 3301 of the holders 331, 332, 333, and 334 may make contact with the object O. In this case, because the slopes 3301S of the fixing portions 3301 make contact with the object (O), the object (O) may feel less discomfort. In addition, surfaces of the fixing portions 3301 of the holders 331, 332, 333, and 334 contacting the object O may be smoothened so as to further reduce any discomfort that the object O may feel. For example, the fixing portions 3301 may include a plastic material or may be coated with a plastic film.

Figure 16:
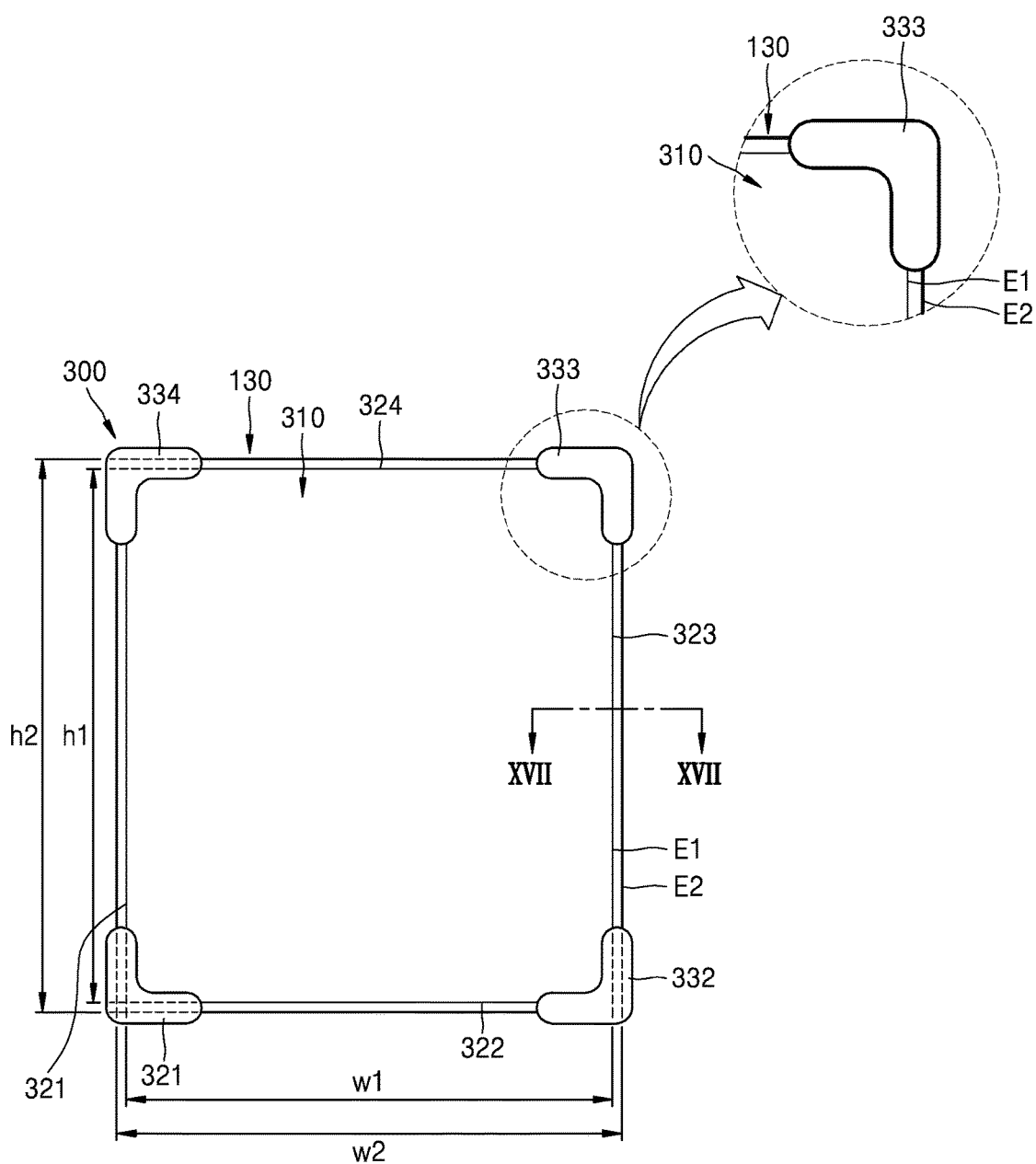
FIG. 16 is a plan view illustrating an X-ray detector to which an X-ray grid structure is attached according to an exemplary embodiment.

FIG. 16 is a plan view illustrating the X-ray detector 130 to which the X-ray grid structure 300 shown in FIG. 4 is attached. Referring to FIGS. 4 and 16, grooves 321, 322, 323, and 324 may be formed in the edges E1 of the X-ray grid 310. The height h1 and width w1 of the X-ray grid 310 may be smaller than the height h2 and width w2 of the X-ray detector 130, respectively. The edges E1 of the X-ray grid 310 may be positioned inside the edges E2 of the X-ray detector 130, and the X-ray grid 310 may be prevented from protruding outward from the X-ray detector 130. This structure may prevent an operator from unstably holding only the X-ray grid 310.

Figure 17:
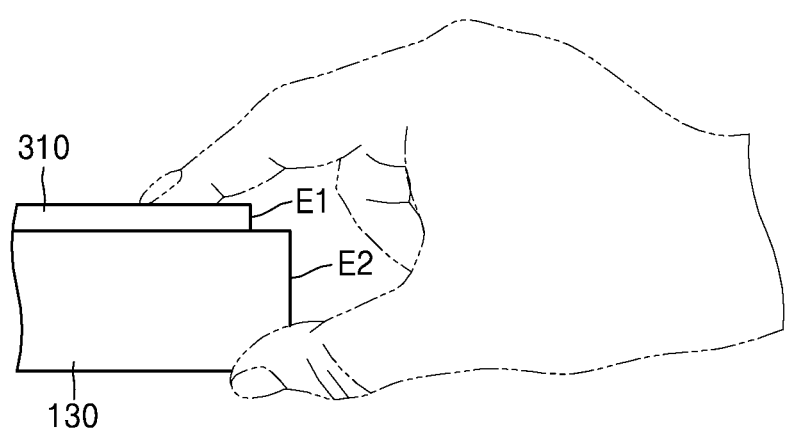
FIG. 17 is a cross-sectional view taken along line XVII-XVII of FIG. 16 according to an exemplary embodiment.

FIG. 17 is a cross-sectional view taken along line XVII-XVII of FIG. 16. Referring to FIG. 17, the edge E1 of the X-ray grid 310 is positioned inside the edge E2 of the X-ray detector 130. Because the X-ray grid 310 is thinner than the X-ray detector 130 is disposed inside the X-ray detector 130, an operator may hold the X-ray grid 310 together with the X-ray detector 130.

If the edges E1 of the X-ray grid 310 are disposed outside or aligned with the edges E2 of the X-ray detector 130, an operator may hold only the X-ray grid 310. In this case, because the X-ray detector 130 is held by only the holders 331, 332, 333, and 334, the holders 331, 332, 333, and 334 may be bent due to the weight of the X-ray detector 130, and thus the X-ray detector 130 may be separated from the holders 331, 332, 333, and 334.

However, according to the exemplary embodiment, the edges E1 of the X-ray grid 310 are disposed inside the edges E2 of the X-ray detector 130. Therefore, when an operator holds the X-ray detector 130 to which the X-ray grid structure 300 is attached, the operator may not only hold the X-ray grid 310.

Reference numerals are used in the accompanying drawings to provide clear understanding of the exemplary embodiments, and terms used in the descriptions of the exemplary embodiments should not be construed as being limited to general meanings or dictionary definitions but should be construed as including all elements that those of ordinary skill in the related art may associate with the terms.

In addition, the above-described operations or exemplary embodiments are examples which are not intended to limit the scope and spirit. In the present disclosure, descriptions of known electric components, control systems, software, and other functional aspects thereof may not given for conciseness. Furthermore, in the drawings, connection lines or members between elements are exemplary functional, physical, and/or electric connections that can be replaced with or used together with other functional, physical, and/or electrical connections. In the present disclosure, terms such as "comprising" and "including" should be construed as open-ended terms that do not exclude the presence or addition of one or more other elements.

In the present disclosure, examples or exemplary terms (for example, "such as" and "etc.") are used for the purpose of description, and thus the scope and spirit are not limited to the examples or exemplary terms unless limited by the claims. Furthermore, it will be understood by those of ordinary skill in the art that various changes in form and details may be made within the exemplary embodiments without departing from the spirit and scope as defined by the following claims.

What is claimed is:

1. An X-ray grid structure configured to be coupled with an X-ray detector, the X-ray grid structure comprising:
   an X-ray grid configured to selectively transmit X-rays to the X-ray detector; and
   a plurality of holders, discrete from the X-ray grid, fixed along an outer edge of the X-ray grid,
   wherein the X-ray grid comprises:
     a first surface configured to receive the X-rays; and
     a second surface opposite to the first surface of the X-ray grid, wherein the X-rays are transmitted from the first surface of the X-ray grid through the second surface of the X-ray grid toward a first surface of the X-ray detector,
   wherein at least one of the plurality of holders comprises:
     a fixing portion fixed to the first surface of the X-ray grid; and
     a support portion configured to be detachably coupled to the X-ray detector and configured to support a second surface of the X-ray detector, the second surface of the X-ray detector being opposite to the first surface of the X-ray detector, and
   wherein the support portion of the at least one of the plurality of holders comprises an elastic material and is configured to be elastically bendable to allow the X-ray grid structure to be detachably coupled to the X-ray detector.

2. The X-ray grid structure of claim 1, wherein the plurality of holders are spaced apart from each other along the outer edge of the X-ray grid.

3. The X-ray grid structure of claim 1, wherein the elastic material comprises at least one of polyurethane and silicone.

4. The X-ray grid structure of claim 1, wherein the X-ray grid has a rectangular shape, and the plurality of holders are disposed at corners of the X-ray grid.

5. The X-ray grid structure of claim 1, wherein the support portion of the at least one of the plurality of holders is configured to be elastically bendable in a direction different from a surface direction of the X-ray grid.

6. An X-ray grid structure configured to be coupled with an X-ray detector, the X-ray grid structure comprising:
   an X-ray grid configured to selectively transmit X-rays to the X-ray detector; and
   a plurality of holders fixed along an outer edge of the X-ray grid,
   wherein at least one of the plurality of holders comprises an elastic material and is configured to be elastically deformable to allow the X-ray grid structure to be detachably coupled to the X-ray detector,
   wherein the at least one of the plurality of holders comprises:
     a fixing portion fixed to the X-ray grid; and
     a support portion configured to be detachably coupled to the X-ray detector and configured to support the X-ray detector, and
   wherein the support portion comprises:
     a rear support portion configured to support a rear side of the X-ray detector which is opposite to a front side of the X-ray detector facing the X-ray grid; and
     a side support portion configured to support a lateral side of the X-ray detector between the front side and the rear side.

7. The X-ray grid structure of claim 6, wherein the fixing portion comprises a slope, so that a height of the fixing portion increases in an outward direction from a center portion of the X-ray grid.

8. The X-ray grid structure of claim 6, wherein the rear support portion comprises a slope, so that a height of the rear support portion increases in an outward direction from a center of the X-ray grid.

9. The X-ray grid structure of claim 6, wherein the elastic material comprises polyurethane.

10. The X-ray grid structure of claim 6, wherein the at least one of the plurality of holders is configured to be elastically deformable in a direction different from a surface direction of the X-ray grid.

11. An X-ray grid structure configured to be coupled with an X-ray detector, the X-ray grid structure comprising:
    an X-ray grid configured to selectively transmit X-rays to the X-ray detector; and
    a plurality of holders fixed along an outer edge of the X-ray grid,
    wherein at least one of the plurality of holders comprises an elastic material and is configured to be elastically deformable to allow the X-ray grid structure to be detachably coupled to the X-ray detector,
    wherein the at least one of the plurality of holders comprises:
      a fixing portion fixed to the X-ray grid; and
      a support portion configured to be detachably coupled to the X-ray detector and configured to support the X-ray detector, and
    wherein the fixing portion is fixed to the X-ray grid using an adhesive.

12. The X-ray grid structure of claim 11, wherein the support portion comprises:
    a rear support portion configured to support a rear side of the X-ray detector which is opposite to a front side of the X-ray detector facing the X-ray grid; and
    a side support portion configured to support a lateral side of the X-ray detector between the front side and the rear side.

13. An X-ray grid structure configured to be coupled with an X-ray detector, the X-ray grid structure comprising:
    an X-ray grid configured to selectively transmit X-rays; and
    a plurality of holders fixed along an outer edge of the X-ray grid,
    wherein at least one of the plurality of holders comprises an elastic material and is configured to be elastically deformable to allow the X-ray grid structure to be detachably coupled to the X-ray detector,
    wherein the X-ray grid comprises:
      a front side facing the X-ray detector and a rear side opposite to the front side; and
      reinforcement films disposed on at least one side of the front side and the rear side of the X-ray grid to reinforce the X-ray grid.

14. An X-ray grid structure comprising:
    an X-ray grid configured to selectively transmit X-rays to an X-ray detector; and a plurality of holders fixed along an outer edge of the X-ray grid, wherein at least one of the plurality of holders comprises an elastic material and is configured to be elastically deformable to allow the X-ray grid structure to be detachably coupled to the X-ray detector, wherein the X-ray grid comprises a front side facing the X-ray detector and a rear side opposite to the front side, and the at least one of the plurality of holders comprises:
- a first member contacting the rear side of the X-ray grid;
- a second member contacting the front side of the X-ray grid; and
- a coupling member fastening the first member and the second member together.

15. The X-ray grid structure of claim 14, wherein the first member comprises at least one coupling hole structure protruding toward the second member for coupling with the coupling member, and the second member comprises a connection hole receiving the coupling member and connected to the at least one coupling hole structure.

16. The X-ray grid structure of claim 15, wherein the coupling member comprises a body portion coupled to the at least one coupling hole structure and a head portion for pressing the second member, and, the body portion comprises a threaded region screwed into the at least one coupling hole structure and a non-threaded region on which a thread is not formed.

17. The X-ray grid structure of claim 14, wherein the second member comprises an elastic material.

18. The X-ray grid structure of claim 17, wherein the first member comprises a material different from a material included in the second member.

19. The X-ray grid structure of claim 18, wherein the first member has a bending strength greater than that of the second member.

20. An X-ray apparatus comprising:
an X-ray radiation unit configured to emit X-rays;
an X-ray detector configured to detect the X-rays having passed through an object; and
an X-ray grid structure which is configured to be coupled with the X-ray detector, and comprises:
- an X-ray grid configured to selectively transmit X-rays to the X-ray detector; and
- a plurality of holders, discrete from the X-ray grid, fixed along an outer edge of the X-ray grid, wherein at least one of the plurality of holders comprises an elastic material and is configured to be elastically deformable to allow the X-ray grid structure to be detachably coupled to the X-ray detector, wherein the at least one of the plurality of holders comprises:
- a fixing portion fixed to the X-ray grid; and
- a support portion configured to be detachably coupled to the X-ray detector and configured to support the X-ray detector, and wherein the support portion comprises:
- a rear support portion configured to support a rear side of the X-ray detector which is opposite to a front side of the X-ray detector facing the X-ray grid; and
- a side support portion configured to support a lateral side of the X-ray detector between the front side and the rear side.

21. An X-ray apparatus of claim 20, wherein the at least one of the plurality of holders is configured to be elastically deformable in a direction different from a surface direction of the X-ray grid.

22. An X-ray apparatus comprising:
an X-ray detector configured to receive X-rays; and
an X-ray grid structure which is configured to filter X-rays, and comprises:
- an X-ray grid configured to filter the X-rays; and
- a first holder, discrete from the X-ray grid, configured to detachably attach the X-ray grid to the X-ray detector, wherein the X-ray grid comprises:
- a first surface configured to receive the X-rays; and
- a second surface opposite to the first surface of the X-ray grid, the second surface being configured to transmit the X-rays received from the first surface of the X-ray grid toward a first surface of the X-ray detector, wherein the first holder comprises:
- a fixing portion fixed to the first surface of the X-ray grid; and
- a support portion configured to be detachably attached to the X-ray detector and configured to support a second surface of the X-ray detector, the second surface of the X-ray detector being opposite to the first surface of the X-ray detector, wherein the support portion of the first holder is made of an elastic material and is configured to be elastically deformable to allow the X-ray grid structure to be detachably attached to the X-ray detector, and wherein the fixing portion and the support portion of the first holder form a C-shape clip in a cross-section.

23. The X-ray apparatus of claim 22, further comprising:
a second holder, a third holder, and a fourth holder, wherein the first holder, the second holder, the third holder, and the fourth holder are each configured to be detachably attached at a corner portion of the X-ray detector and the X-ray grid.

24. The X-ray apparatus of claim 22, wherein the X-ray grid structure is attached to the X-ray detector such that the X-ray grid is disposed between the X-ray detector and an X-ray emitter.

25. An X-ray apparatus of claim 22, wherein the support portion of the at least one of the plurality of holders is configured to be elastically bendable in a direction different from a surface direction of the X-ray grid.

* * * * *